United States Patent
DiNardo et al.

(10) Patent No.: US 10,492,790 B2
(45) Date of Patent: Dec. 3, 2019

(54) APPARATUS AND METHOD FOR CINCHING A STRAIGHT STAPLE LINE

(71) Applicant: Ethicon Endo-Surgery, LLC, Guaynabo, PR (US)

(72) Inventors: Brian F. DiNardo, Cincinnati, OH (US); Charles J. Scheib, Loveland, OH (US); Frederick E. Shelton, IV, Hillsboro, OH (US); Christopher C. Miller, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 655 days.

(21) Appl. No.: 14/863,999

(22) Filed: Sep. 24, 2015

(65) Prior Publication Data

US 2017/0086847 A1   Mar. 30, 2017

(51) Int. Cl.
*A61B 17/115* (2006.01)
*A61B 17/068* (2006.01)
(Continued)

(52) U.S. Cl.
CPC ........ *A61B 17/1155* (2013.01); *A61B 17/068* (2013.01); *A61B 17/07207* (2013.01);
(Continued)

(58) Field of Classification Search
CPC ........ A61B 17/068; A61B 2017/07271; A61B 17/105; A61B 17/1155; A61B 2017/0053;
(Continued)

(56) References Cited

U.S. PATENT DOCUMENTS

| 4,805,823 A | 2/1989 | Rothfuss |
| 5,205,459 A | 4/1993 | Brinkerhoff et al. |

(Continued)

FOREIGN PATENT DOCUMENTS

| CN | 104 434 252 A | 3/2015 |
| EP | 0 770 356 A1 | 5/1997 |

(Continued)

OTHER PUBLICATIONS

European Search Report, Extended, and Written Opinion with Annex dated Feb. 22, 2017 for Application No. EP 16190334.9, 51 pgs.

(Continued)

*Primary Examiner* — Robert F Long
(74) *Attorney, Agent, or Firm* — Frost Brown Todd LLC

(57) ABSTRACT

An apparatus includes an end effector including an anvil and lower jaw. The anvil is pivotable toward the lower jaw to capture tissue. The apparatus further includes a stapling and severing assembly configured to sever and staple tissue clamped between the anvil and the lower jaw. A staple cartridge is coupled with the lower jaw. The staple cartridge includes a deck facing the anvil, a plurality of staples positioned in a plurality of staple openings formed through the deck, and a cinching feature positioned on the deck. At least a portion of the cinching feature is configured to be captured by the staples as the staples are driven out of the staple openings in response to activation of the stapling and severing mechanism. The cinching feature is configured to cinch severed and stapled tissue.

20 Claims, 24 Drawing Sheets

(51) Int. Cl.
  *A61B 17/10* (2006.01)
  *A61B 17/072* (2006.01)
  *A61B 17/04* (2006.01)
  *A61B 17/11* (2006.01)
  *A61B 17/00* (2006.01)
  *A61B 17/06* (2006.01)

(52) U.S. Cl.
  CPC ...... *A61B 17/07292* (2013.01); *A61B 17/105* (2013.01); *A61B 17/0482* (2013.01); *A61B 17/0487* (2013.01); *A61B 17/06166* (2013.01); *A61B 17/1114* (2013.01); *A61B 2017/00398* (2013.01); *A61B 2017/00734* (2013.01); *A61B 2017/0464* (2013.01); *A61B 2017/07271* (2013.01); *A61B 2017/1142* (2013.01)

(58) Field of Classification Search
  CPC ............ A61B 17/0401; A61B 17/0469; A61B 17/07292; A61B 17/07207; A61B 17/06166; A61B 2017/1142; A61B 2017/0464; A61B 2017/00734; A61B 2017/00398; A61B 17/0487; A61B 17/0482; A61B 17/1114
  USPC ............................................ 227/175.1–182.1
  See application file for complete search history.

(56) References Cited

U.S. PATENT DOCUMENTS

| | | | |
|---|---|---|---|
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,415,334 A | 5/1995 | Williamson et al. | |
| 5,465,895 A | 11/1995 | Knodel et al. | |
| 5,503,638 A * | 4/1996 | Cooper ............ | A61B 17/07207 606/148 |
| 5,533,661 A | 7/1996 | Main et al. | |
| 5,597,107 A | 1/1997 | Knodel et al. | |
| 5,632,432 A | 5/1997 | Schultze et al. | |
| 5,673,840 A | 10/1997 | Schultze et al. | |
| 5,704,534 A | 1/1998 | Huitema et al. | |
| 5,814,055 A | 9/1998 | Knodel et al. | |
| 5,902,312 A * | 5/1999 | Frater ............ | A61B 17/07207 606/148 |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,794,475 B2 | 9/2010 | Hess et al. | |
| 8,408,439 B2 | 4/2013 | Huang et al. | |
| 8,453,914 B2 | 6/2013 | Laurent et al. | |
| 8,910,847 B2 | 12/2014 | Nalagatla et al. | |
| 9,138,225 B2 | 9/2015 | Huang et al. | |
| 9,161,803 B2 | 10/2015 | Yates et al. | |
| 9,289,207 B2 | 3/2016 | Shelton, IV | |
| 9,463,022 B2 | 10/2016 | Swayze et al. | |
| 9,498,222 B2 | 11/2016 | Scheib et al. | |
| 9,775,617 B2 * | 10/2017 | Carter ............ | A61B 17/07292 |
| 2005/0059996 A1 * | 3/2005 | Bauman ............... | A61B 17/072 606/215 |
| 2007/0010866 A1 * | 1/2007 | Dann ............... | A61B 17/00234 623/1.11 |
| 2007/0246505 A1 * | 10/2007 | Pace-Floridia ............ | A61B 17/07207 227/175.1 |
| 2009/0134200 A1 * | 5/2009 | Tarinelli ........... | A61B 17/07207 227/180.1 |
| 2010/0065606 A1 * | 3/2010 | Stopek ................. | A61B 17/072 227/176.1 |
| 2010/0243711 A1 * | 9/2010 | Olson ............... | A61B 17/07207 227/181.1 |
| 2011/0087279 A1 * | 4/2011 | Shah ................ | A61B 17/07207 606/219 |
| 2012/0150206 A1 * | 6/2012 | Barikosky ........ | A61B 17/07292 606/153 |
| 2012/0234900 A1 * | 9/2012 | Swayze ............ | A61B 17/07207 227/180.1 |
| 2012/0273547 A1 * | 11/2012 | Hodgkinson .... | A61B 17/07207 227/176.1 |
| 2013/0153634 A1 * | 6/2013 | Carter ................... | A61B 17/072 227/176.1 |
| 2013/0193186 A1 * | 8/2013 | (Tarinelli) Racenet ..................... | A61B 17/07207 227/175.1 |
| 2013/0193190 A1 * | 8/2013 | Carter ............ | A61B 17/07292 227/179.1 |
| 2014/0131418 A1 * | 5/2014 | Kostrzewski .......... | A61B 17/32 227/176.1 |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166728 A1 | 6/2014 | Swayze et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2015/0305743 A1 * | 10/2015 | Casasanta ............ | A61B 17/105 227/176.1 |
| 2015/0351761 A1 * | 12/2015 | Shelton, IV ..... | A61B 17/07292 606/219 |
| 2015/0351764 A1 * | 12/2015 | Shelton, IV ..... | A61B 17/00491 227/176.1 |
| 2016/0374666 A1 | 12/2016 | DiNardo et al. | |
| 2016/0374670 A1 | 12/2016 | Fox et al. | |

FOREIGN PATENT DOCUMENTS

| | | |
|---|---|---|
| EP | 2 008 595 A2 | 12/2008 |
| EP | 2 452 634 A2 | 5/2012 |
| EP | 2 614 786 A1 | 7/2013 |
| EP | 2 954 857 A1 | 12/2015 |
| WO | WO 2014/139419 A1 | 9/2014 |
| WO | WO 2015/146548 A1 | 4/2017 |

OTHER PUBLICATIONS

European Examination Report dated May 18, 2018 for Application No. EP 16190334.9, 5 pgs.

International Search Report and Written Opinion dated Dec. 8, 2016 for Application No. PCT/US2016/052116, 16 pgs.

* cited by examiner

APPARATUS AND METHOD FOR CINCHING A STRAIGHT STAPLE LINE

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
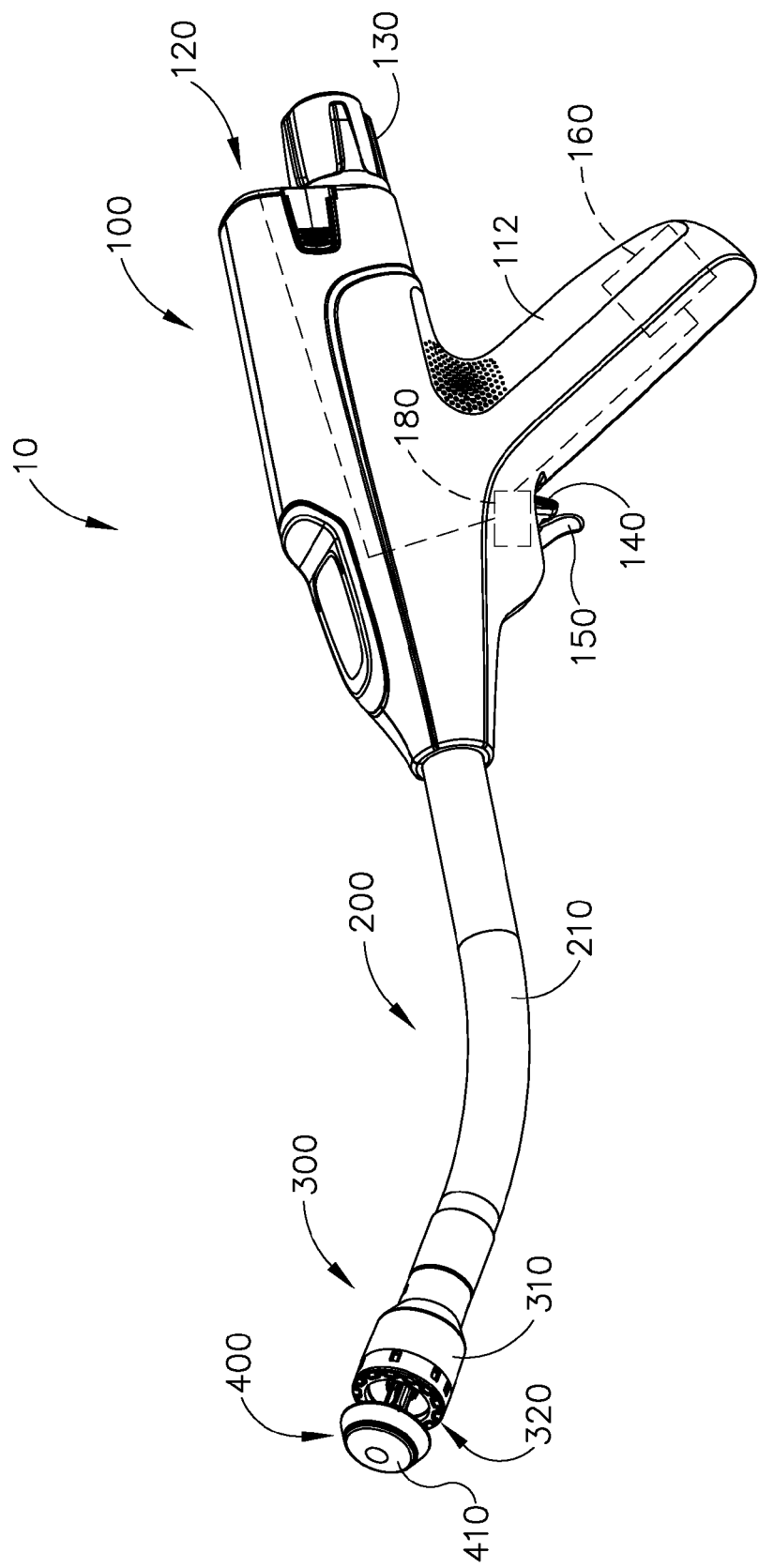
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. OVERVIEW OF EXEMPLARY CIRCULAR STAPLING SURGICAL INSTRUMENT

Figure 2:
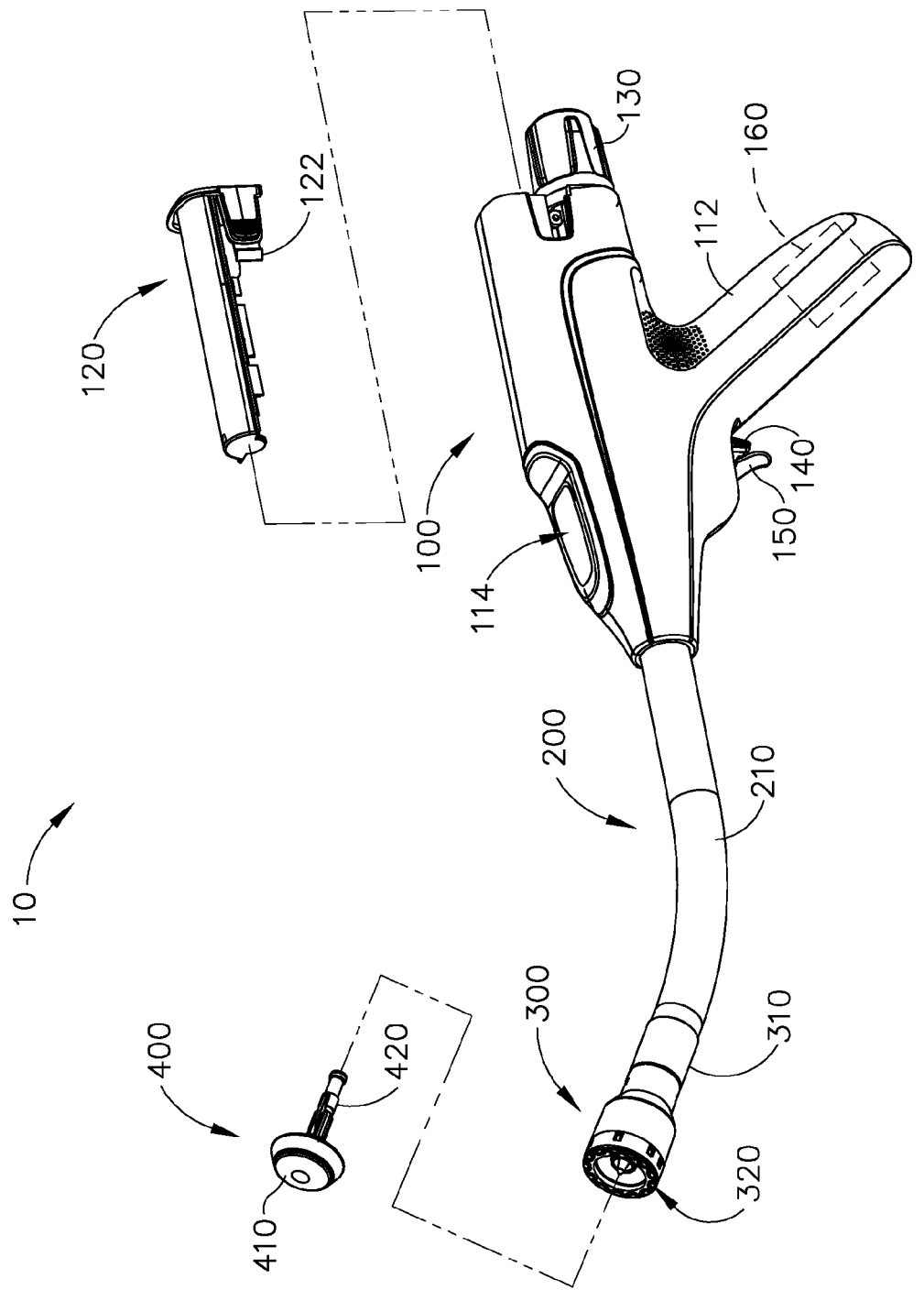
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,506, entitled "Anvil Stabilization Features for Surgical Stapler," filed Jun. 26, 2015, issued as U.S. Pat. No. 10,271,842 on Apr. 30, 2019; U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
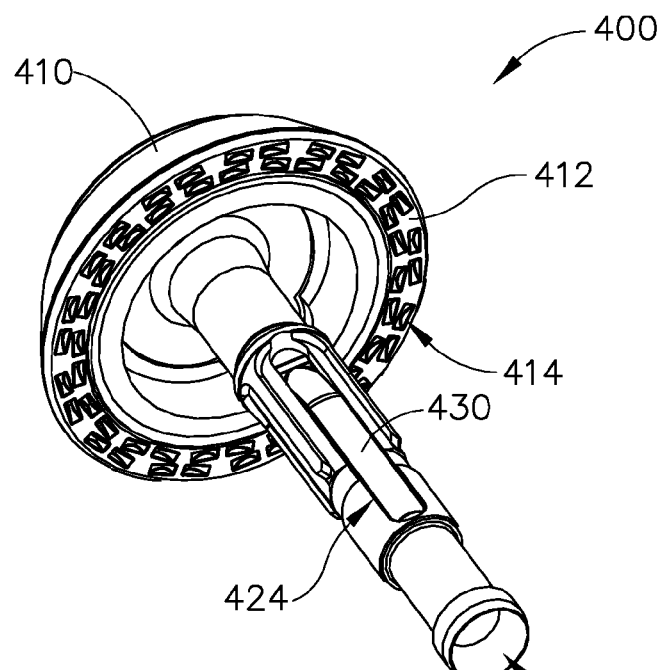
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
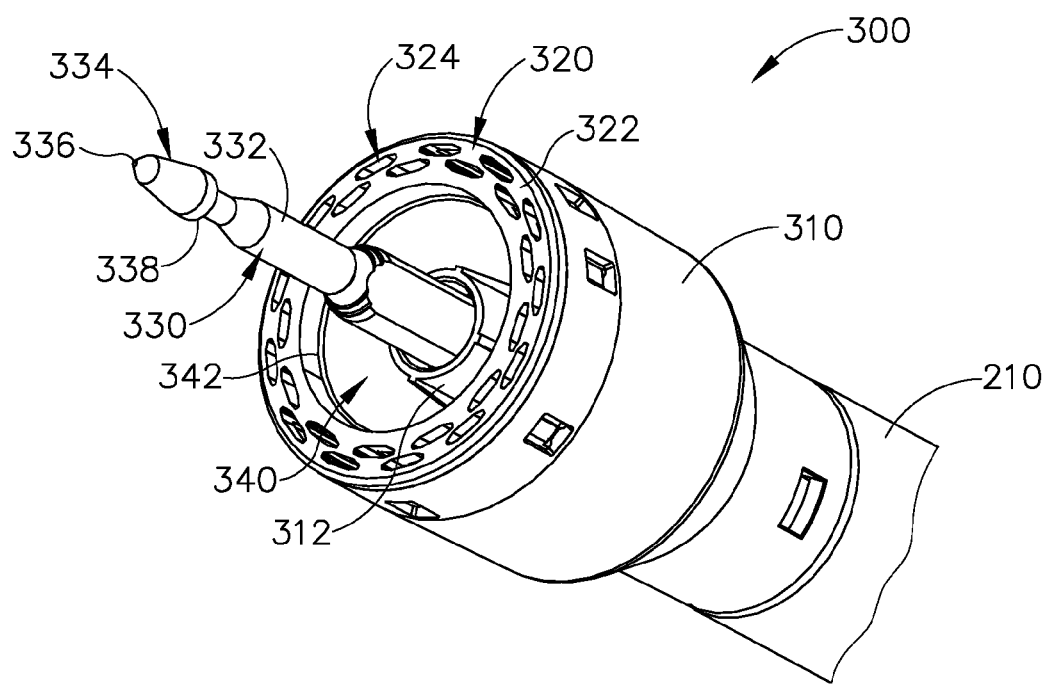
FIG. 4 depicts a perspective view of the stapling head assembly of the circular stapler of FIG. 1.
Figure 5:
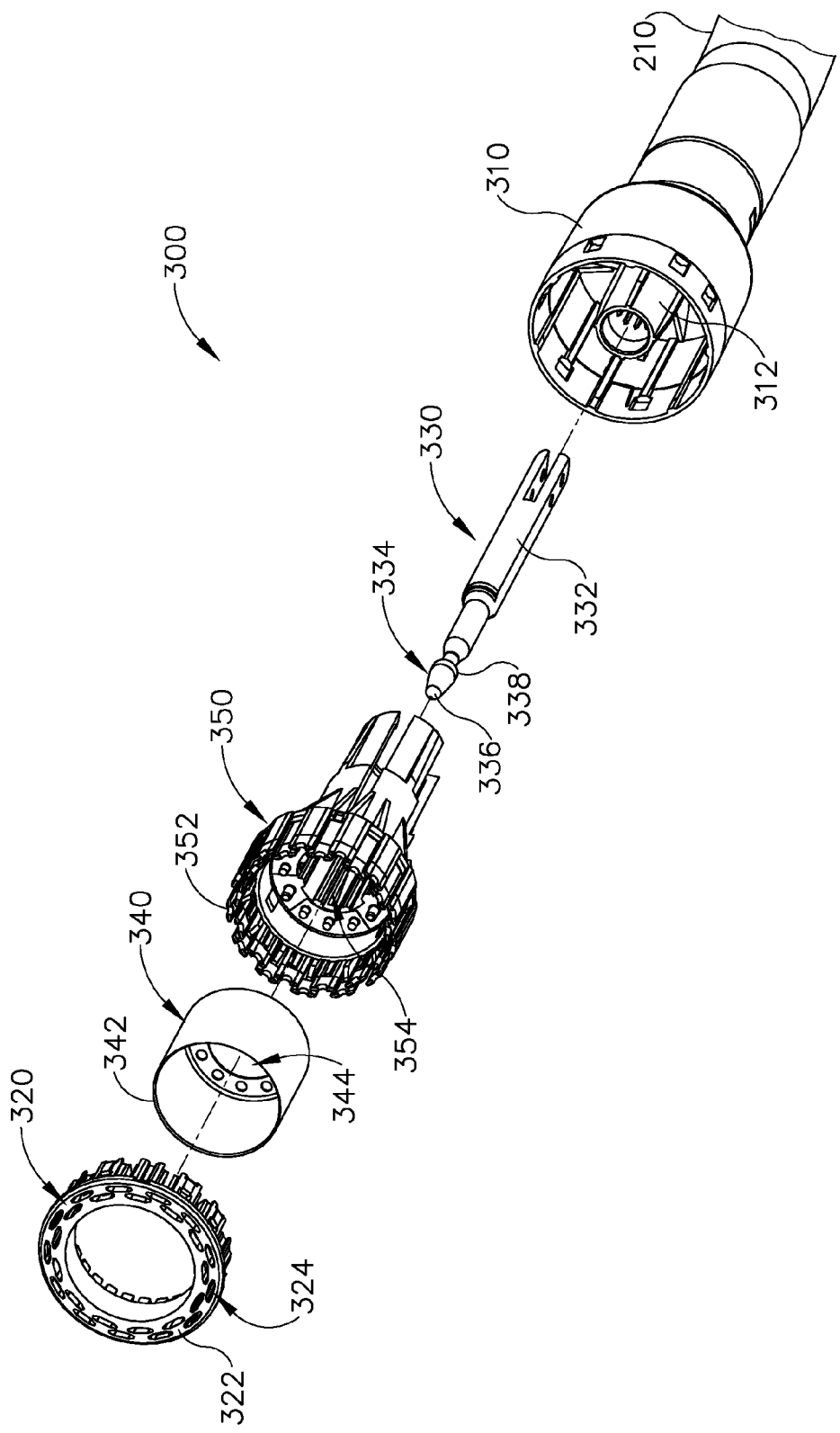
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
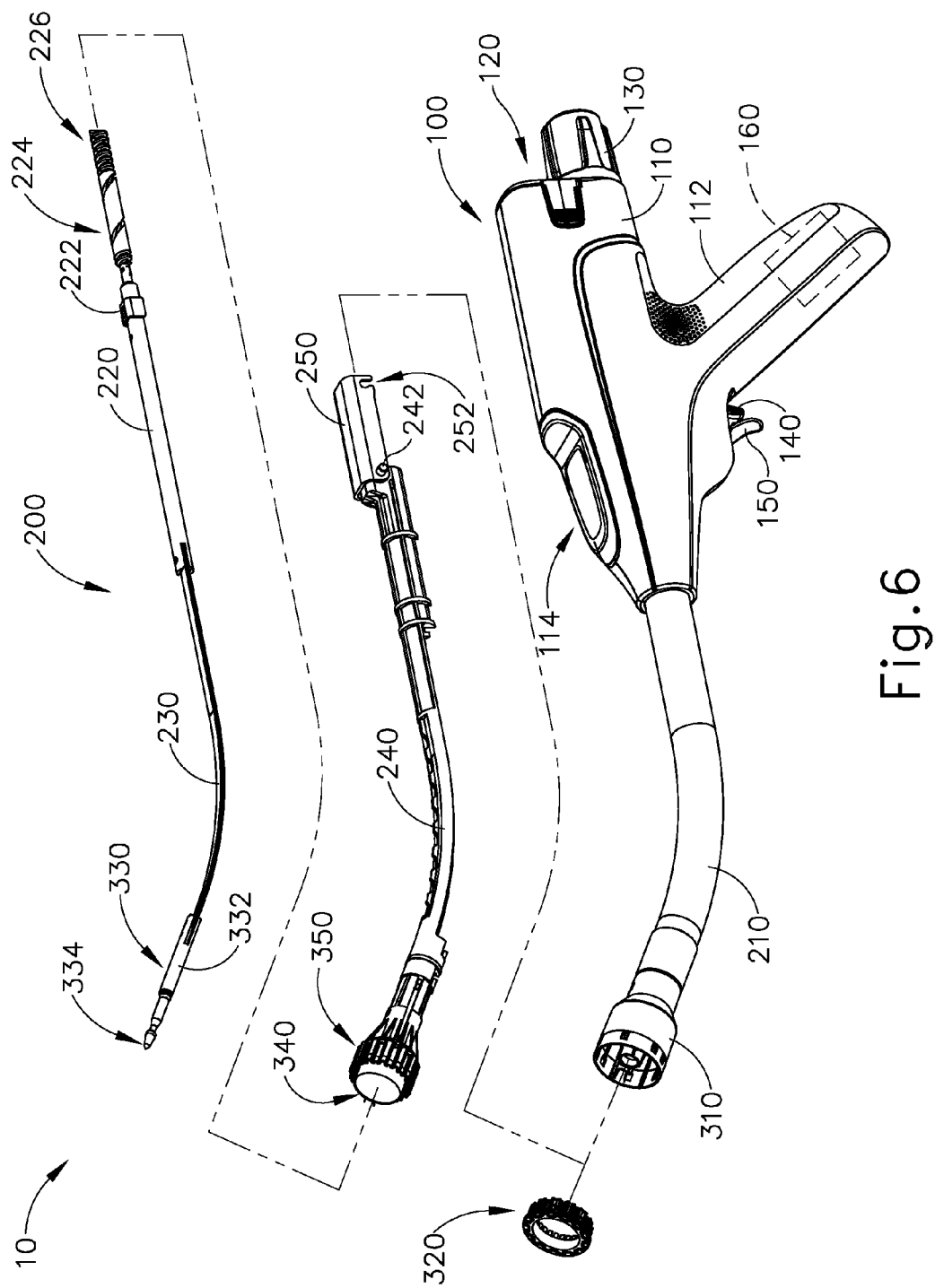
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section that is configured to facilitate positioning of stapling head assembly (300) within a patient's colon.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance between opposing surfaces (412, 322) of anvil (400) and stapling head assembly (300) until a suitable gap distance has been achieved.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, published as U.S. Pub. No. 2016/0374666 on Dec. 29, 2016, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7-10 show an exemplary surgical procedure for providing a surgical anastomosis using instrument (10). In various instances, an anastomosis may be performed to remove a section of a patient's gastrointestinal (GI) tract. In the present example, multiple portions of a patient's colon are severed and stapled to resect a diseased portion (C') of the colon (C). The remaining severed and stapled portions of colon (C) are then anastomosed together, as discussed in further detail below.

Figure 7:
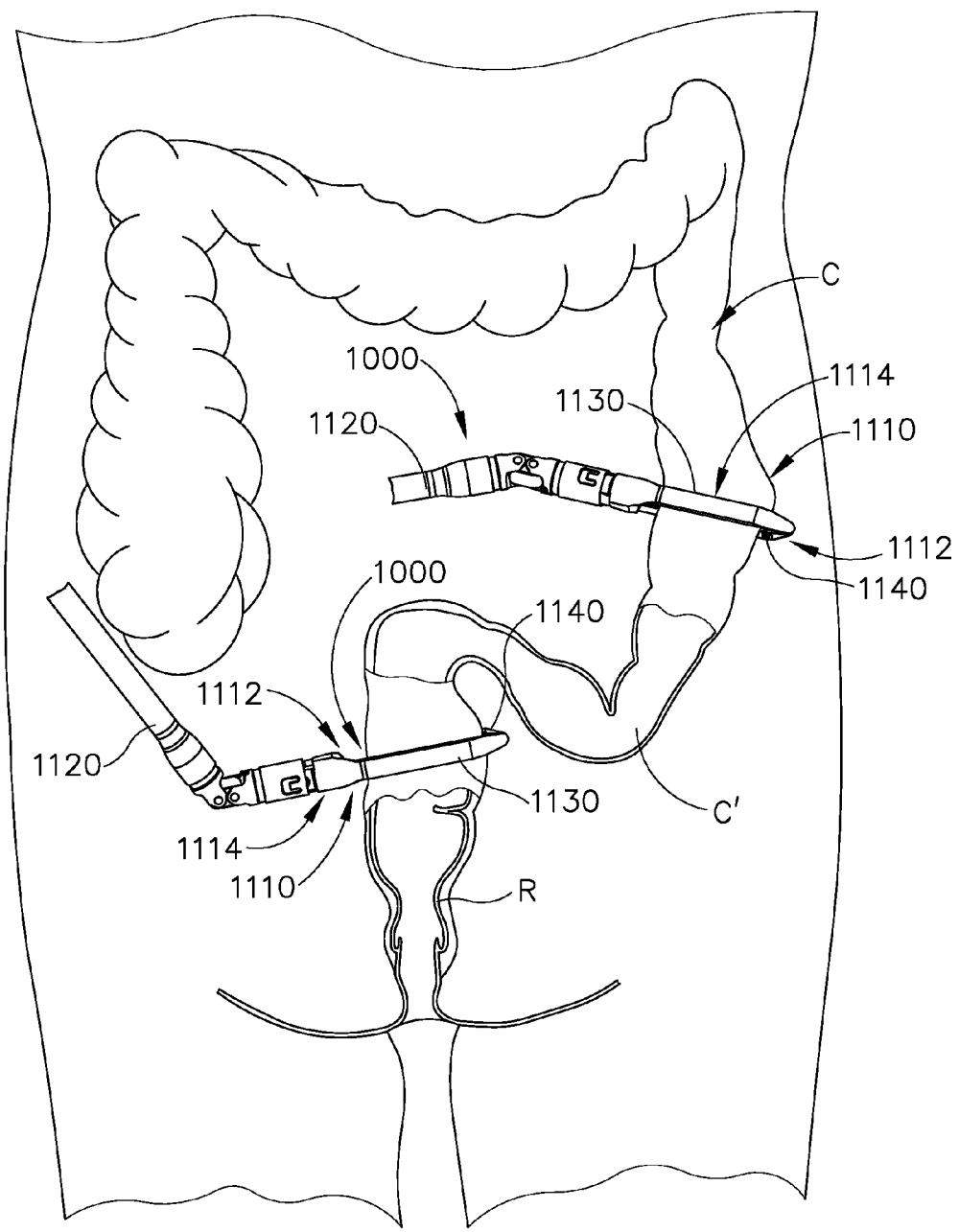
FIG. 7 depicts a schematic view of a lower portion of a patient's gastrointestinal tract, with an endocutter stapler being utilized to staple and sever the gastrointestinal tract at a first location and the endocutter stapler being utilized to staple and sever the gastrointestinal tract at a second location, thereby dividing the gastrointestinal tract into an upper portion, a transected portion, and a lower portion during a surgical procedure.

As shown in FIG. 7, multiple endocutter staplers (1000) may be inserted into a patient to sever and staple portions of the patient's colon (C). By way of example only, endocutter staplers (1000) may be constructed and operable in accordance with at least some of the teachings of U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380, 695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

In the example shown, endocutter staplers (1000) are inserted into the body laparoscopically via respective trocars. Endocutter stapler (1000) comprises a shaft (1120) and an end effector (1110) extending from the shaft (1120). End effector (1110) comprises a first jaw (1112) and a second jaw (1114). First jaw (1112) comprises a staple cartridge (1140). Staple cartridge (1140) is insertable into and removable from first jaw (1112), though some variations may provide a staple cartridge that is not removable from (or at least readily replaceable from) first jaw (1112). Second jaw (1114) comprises an anvil (1130) that is configured to deform staples ejected from staple cartridge (1140). Second jaw (1114) is pivotable relative to first jaw (1112), though some variations pay provide first jaw (1112) as being pivotable relative to the second jaw (1114). Endocutter staplers (1000) may be configured ad operable in accordance with at least some of the teachings of U.S. Pub. No. 2013/0168435, entitled "Surgical Stapling Instrument with an Articulatable End Effector," published Jul. 4, 2013, issued as U.S. Pat. No. 9,138,225 on Sep. 22, 2015, the disclosure of which is incorporated by reference. While end effector (1110) is straight and is thus configured to apply a straight line of staples (185) in the present example, in other examples end effector (1110) may be curved and may thus apply a curved line of staples (185).

Figure 8:
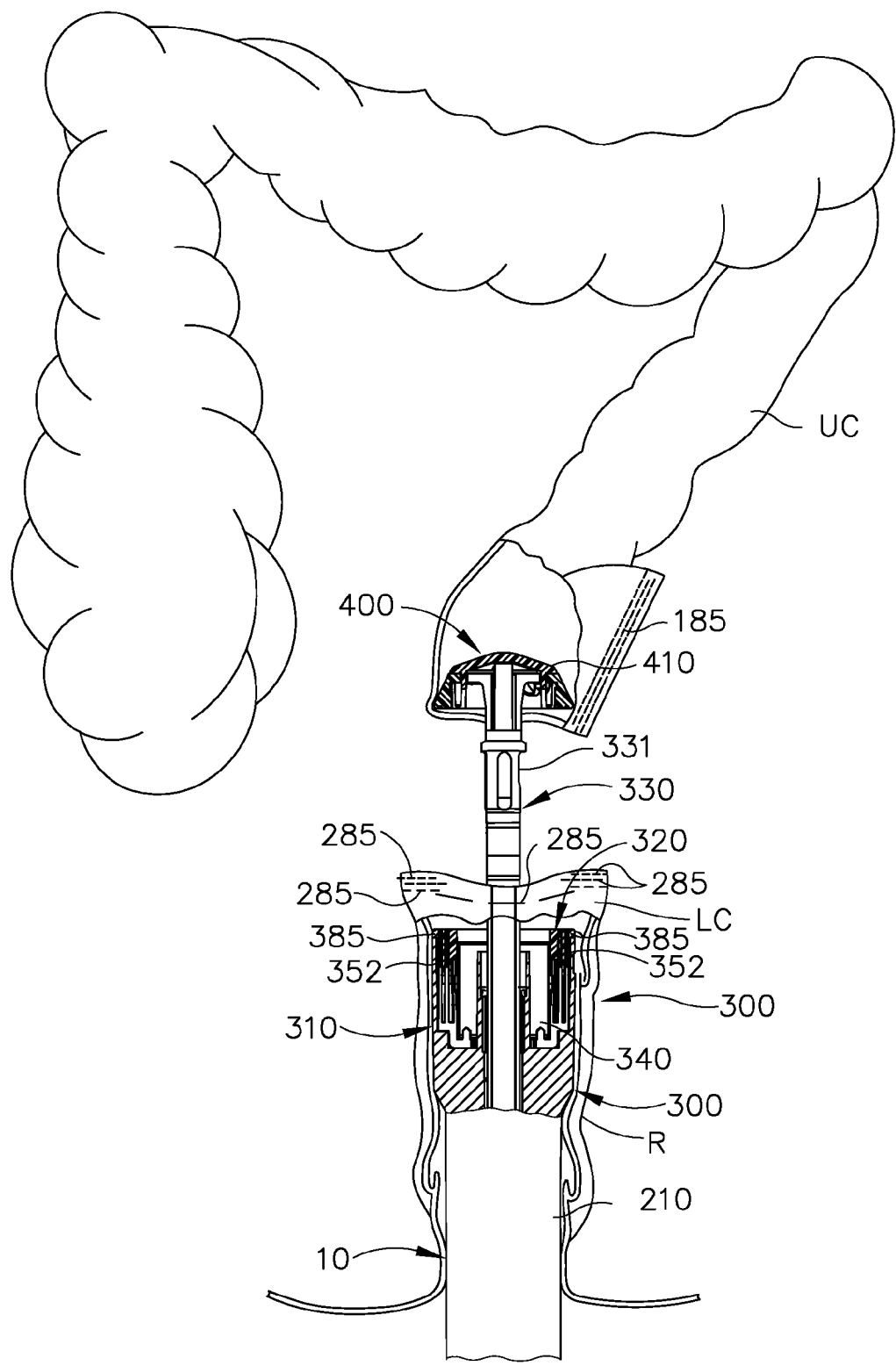
FIG. 8 depicts a schematic view of the gastrointestinal tract of FIG. 7 during another step of the surgical procedure of FIG. 7, showing the anvil of FIG. 3 positioned in the upper portion of the gastrointestinal tract and the stapling head assembly of FIG. 4 positioned in the lower portion of the gastrointestinal tract, with the anvil and the stapling head assembly and adjacent regions of the gastrointestinal tract shown in cross-section.
Figure 9:
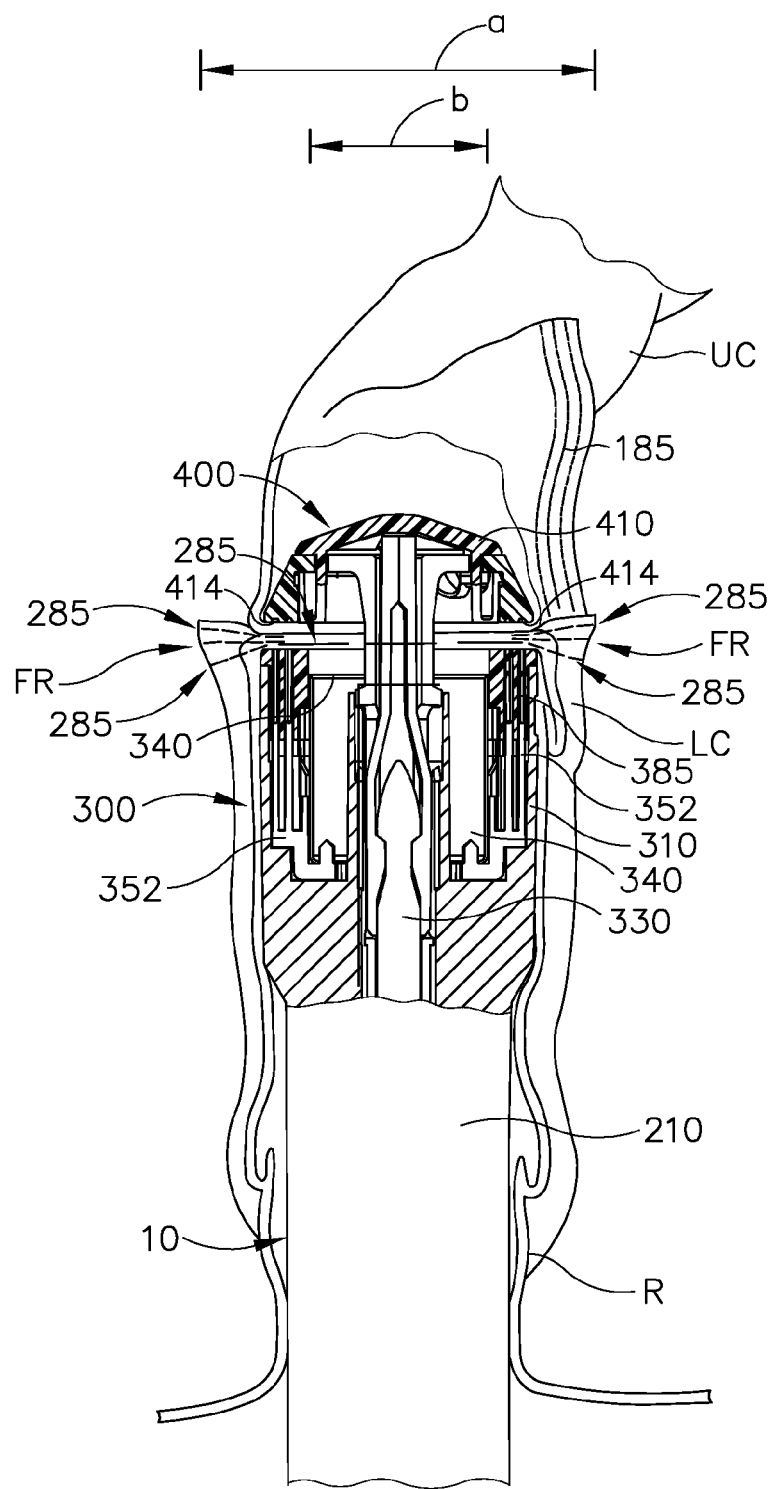
FIG. 9 depicts a schematic view of the gastrointestinal tract of FIG. 7 during another step of the surgical procedure of FIG. 7, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.
Figure 10:
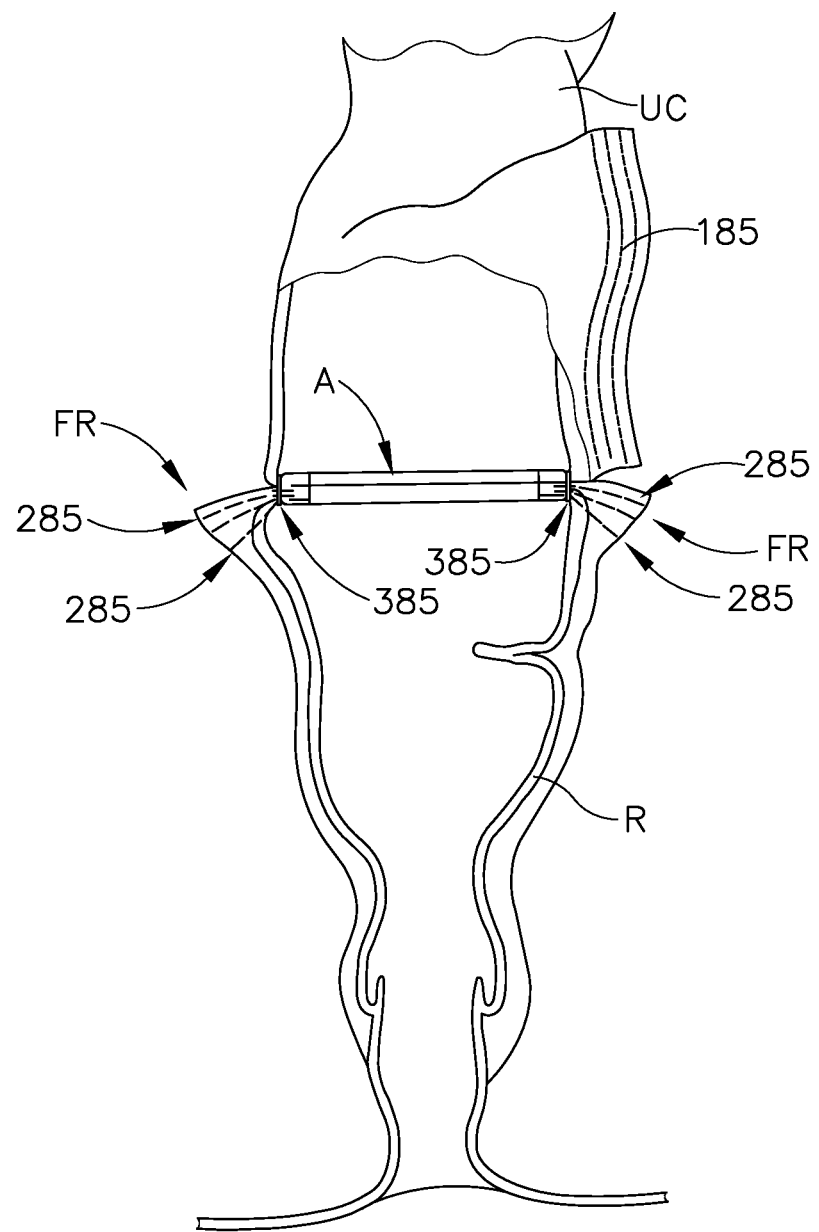
FIG. 10 depicts a schematic view of the gastrointestinal tract of FIG. 7 upon completion of the surgical procedure of FIG. 7, with the upper and lower portions of the patient's gastrointestinal tract joined by staples deployed from the circular stapler of FIG. 1, providing an anastomosis between the upper and lower portions of the patient's gastrointestinal tract, with the anastomosis and adjacent regions of the gastrointestinal tract shown in cross-section.

Anvil (1130) of endocutter stapler (1000) can be opened such that anvil (1130) and staple cartridge (1140) of endocutter stapler (1000) are positioned relative to the patient's colon (C). When anvil (1130) is moved into a closed position, anvil (1130) clamps the colon (C) against staple cartridge (1140). Turning now to FIG. 7, endocutter stapler (1000) can be operated to sever and staple the colon (C) at a first, or upper, location. In the example shown, three linear rows of staples (185) are implanted on the upper side of the severed upper portion (UC) of colon (C) and three rows of the staples (185) are implanted in the adjacent region of the diseased portion (C') of the colon (C). The same endocutter stapler (1000) (if reloaded with another cartridge (1140)), or another endocutter stapler (1000), can be operated to sever and staple the colon (C) at a second, or lower, location. In the present example, three linear rows of staples (285) implanted on the lower side of the severed lower portion (LC) of the colon (C) and three rows of staples (285) are implanted in the adjacent region of the diseased portion (C') of the colon (C). However, in other examples, other suitable configurations of staples may be implanted onto the upper portion (UC) and/or the lower portion (LC) of the colon (C). Once the colon (C) has been transected and stapled at the upper location and the lower location, the diseased portion (C') of the colon can be removed from the patient, as illustrated in FIGS. 8-10.

Referring again to FIGS. 8-9, circular stapler (10) may be utilized to anastomose the upper portion (UC) and the lower portion (LC) of the colon (C). An operator inserts a portion of shaft (210) and stapling head assembly (300) into the rectum (R) of the patient into the lower portion (LC) of the colon (C). In the example shown, a user then inserts trocar (330) through the rows of staples (285). Trocar (330) of circular stapler (10) may then be positioned in the upper portion of the colon C. In various instances, the sidewall of the upper portion of the colon C can be incised and trocar (330) can then be positioned inside the upper portion. Anvil (400) may then be directed into the upper portion of the colon (C) and connected to trocar (330) in the manner discussed above and as shown in FIG. 8.

The operator may then draw anvil (400) toward stapling head assembly (300), in the manner described above (e.g., utilizing knob (130), thus also drawing the upper colon portion (UC) toward the lower colon portion (LC). The operator may then retract trocar (330) until the tissue of the upper colon portion (UC) and the lower colon portion (LC) are compressed against deck (320) as shown in FIG. 9. It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces of anvil (400) and stapling head assembly (300) until a suitable gap distance has been achieved, such as in the manner discussed in U.S. patent application Ser. No. 14/751,506, issued as U.S. Pat. No. 10,271,842 on Apr. 30, 2019, the disclosure of which is incorporated by reference herein. As shown in FIG. 9, flap regions (FR) are formed in the lower portion (LC) of the colon (C) as anvil (400) is drawn toward stapling head assembly (300). These flap regions (FR) extend outwardly from the region of tissue compressed between anvil (400) and stapling head assembly (300).

As discussed above, stapling head assembly (300) is configured to apply annular arrays of staples (385) in the tissue captured between anvil (400) and stapling head assembly (300). Knife member (340) is advanced toward anvil (440) to sever the tissue positioned radially inwardly with respect to the annular arrays of staples (385) applied by circular stapling instrument (10). After the staples (385) have been fired and tissue has been severed, anvil (400) and stapling head assembly (300) may together be withdrawn from the patient's rectum (R). The incision that was used to insert anvil (400) into the upper portion (UC) of the colon (C) may be closed via suturing or using any other suitable technique.

As shown in FIG. 10, the upper portion (UC) of the colon (C) and the lower portion (LC) of the colon (C) are held together by the annular array of staples (385) deployed by circular stapling instrument (10). The deployed annular array of staples (385) forms an anastomosis (A) that allows fluid tight communication from the upper portion (UC) of the colon (C) to the lower portion (LC) of the colon (C). Some of staples (285) that were deployed by endocutter stapler (1000) will be removed with the tissue that was transected by knife member (340) during actuation of stapling head assembly (300). However, in this example, there are some staples (285) remaining in the outwardly projecting flap regions (FR) in the lower portion (LC) of the colon (C), outside of the anastomosis (A). This is due to the fact that the flap regions (FR) define a width (a) that is substantially greater than the diameter (b) of knife member (340), as best seen in FIG. 9. The flap regions (FR) may nevertheless remain sealed by those remaining staples (285).

II. EXEMPLARY ALTERNATIVE STAPLE CARTRIDGES

In some instances, staples (385) that were deployed by circular stapling instrument (10) may overlap with at least some of staples (285) that were deployed by endocutter stapler (1000) in the procedure described above with reference to FIGS. 7-10. Such overlap may prevent proper formation of staples (385), which may compromise the integrity of anastomosis (A) in the long term. In addition or in the alternative, at least some of staples (285) that were deployed by endocutter stapler (1000) may interfere with compression of tissue between anvil (400) and deck member (320) and/or the traversal of knife member (340) through the tissue, which may also compromise the integrity of anastomosis (A) in the long term. Furthermore, there may be instances where the seal provided by staples (285) in flap regions (FR) of the lower portion (LC) of the colon (C) may eventually fail over time. It may therefore be desirable to provide features that prevent the outward extension of flap regions (FR) and position all of staples (285) and flap regions (FR) within the diameter (b) of knife member (340). Various examples of such features will be described in greater detail below.

A. Exemplary Alternative Staple Cartridge Including Suture and Suture Retainers

Figure 11:
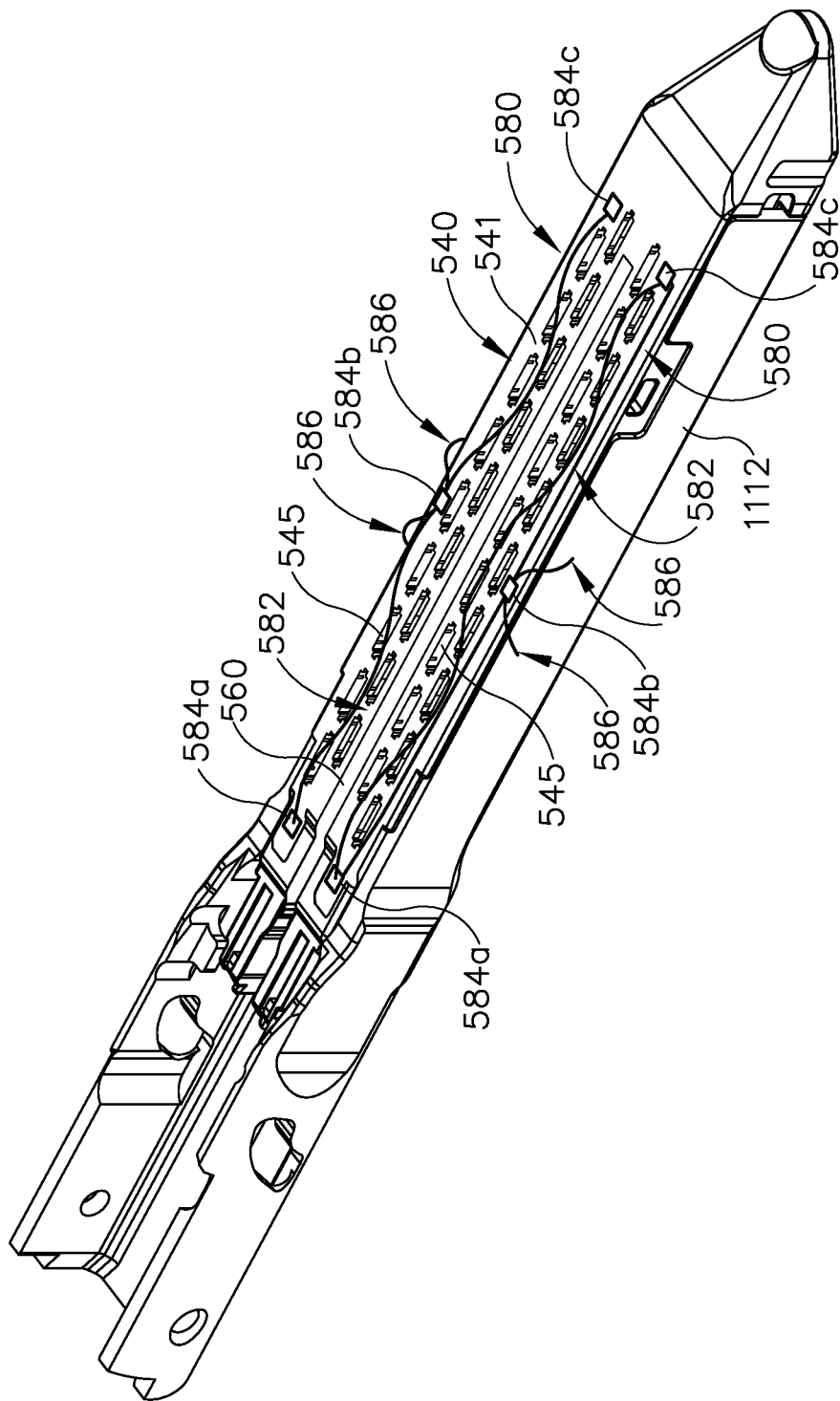
FIG. 11 depicts a perspective view of an exemplary alternative staple cartridge loaded into the lower jaw of the stapling device of FIG. 7, including a suture on a deck thereof, capable of being utilized in the procedure shown in FIGS. 7-10.

FIG. 11 shows an exemplary alternative staple cartridge (540) inserted in first jaw (1112) of end effector (1110). Staple cartridge (540) is substantially similar to staple cartridge (1140), except that staple cartridge (540) includes two rows of staple cavities (545) on each side of slot (560) of instead of three rows. Therefore, when staple cartridge (540) is incorporated into end effector (1110), two rows of staples (585) are implanted onto opposing, severed portions of tissue rather than three rows of staples (585). Moreover, staple cartridge (540) includes a suture assembly (580) on each side of slot (560). Each suture assembly comprises a length of suture (582), a proximal suture retainer (584a), a middle suture retainer (584b), and a distal suture retainer (584c). In the present example, suture (582) comprises any suitable monofilament or polyfilament material as will be apparent to persons skilled in the art in view of the teachings herein.

Figure 12:
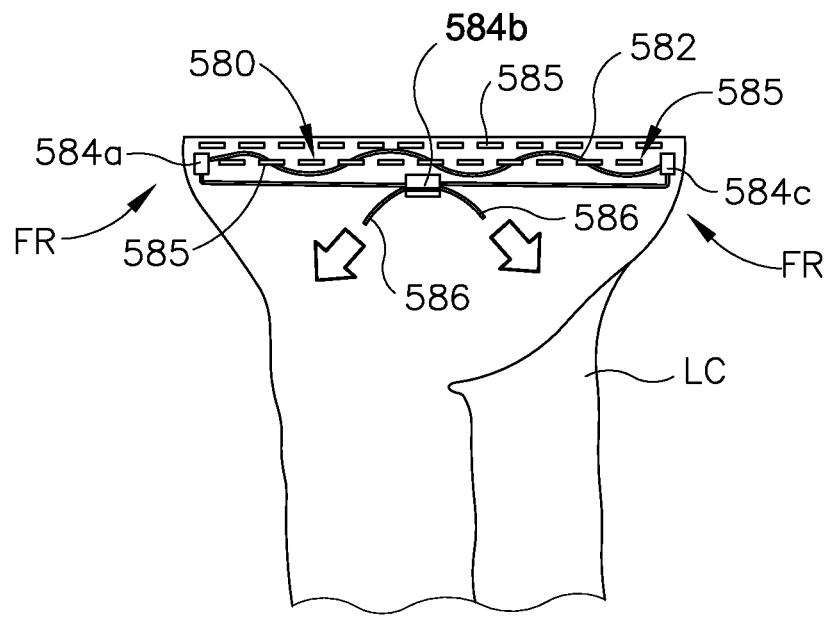
FIG. 12 depicts a side elevational view of portion of the gastrointestinal tract after having been stapled and severed utilizing the staple cartridge of FIG. 11.

In the example shown, at least a portion of suture assembly (580) is removably adhered to cartridge deck (541). However, in other examples, suture assembly (580) may be affixed to cartridge deck (541) according to other suitable methods. As shown, each suture (582) extends along cartridge deck (541) in a wave-like configuration such that the suture (582) extends over alternating staple cavities (545) nearest the outer edges of jaw (1112). Suture (582) slidably extends through proximal and distal suture retainers (584, 584c), with the free ends (586) of suture (582) passing through middle suture retainer (584b) in a crisscross confiruration. Suture (582) thus forms a loop. It should be understood that only one half of the loop formed by suture (582) passes through middle suture retainer (584b) to reach distal suture retainers (584, 584c); while the other half of the loop formed by suture (582) does not pass through middle suture retainer (584b) to reach distal suture retainers (584, 584c). This relationship is best seen in FIG. 12, which shows suture assembly (580) deployed in tissue. It should be understood that the half of the loop formed by suture (582) that passes through middle suture retainer (584b) to reach distal suture retainers (584, 584c) is spaced laterally away from staple cavities (545). Thus, when staple cartridge (540) is actuated, staples (585) will not engage the half of the loop formed by suture (582) that passes through middle suture retainer (584b).

Middle suture retainer (584b) includes internal features that allow free ends (586) to be pulled away from middle suture retainer (584), thereby allowing an operator to reduce the length of the loop formed by suture (582); yet those internal features of middle suture retainer (584b) prevent the free ends (586) to be pulled back through middle suture retainer (584). In other words, middle suture retainer (584b) provides one-way passage for each free end (586), only allowing the length of the loop formed by suture (582) to be reduced; without allowing the length of the loop formed by suture (582) to be increased. Various suitable forms that may be used to form the internal structures of middle suture retainer (584b) in order to provide such functionality will be apparent to those of ordinary skill in the art in view of the teachings herein.

As end effector (1100) containing staple cartridge (540) is actuated, drivers of staple cartridge (540) eject staples (585) out of cavities (545) toward anvil (1130), causing portions of suture (582) overlying cavities (545) to be captured by crowns of staples (585). Thus, as staples (585) are formed, portions of suture (582) are captured amongst the formed staples (585) and coupled to the severed and stapled tissue, as shown in FIG. 12. In the example shown, suture (582) is coupled to the tissue via alternating (i.e., every other) staple crowns such that suture (582) may slide relative to staples (585) and tissue. Suture retainers (584a, 584c) are also secured to the tissue in this example. In particular, suture retainers (584a, 584c) are secured to the outer ends of flap regions (FR) are formed in the lower portion (LC) of the colon (C). By way of example only, suture retainers (584a, 584c) may include cleats, barbs, adhesive, and/or other features that assist in securing suture retainers (584a, 584c) to the tissue in response to clamping of the tissue in end effector (1100). Various suitable ways in which suture retainers (584a, 584c) may be secured to the tissue will be apparent to those of ordinary skill in the art in view of the teachings herein. In the present example, middle suture retainer (584b) is not secured to the tissue, though middle suture retainer (584b) may be secured to tissue in some other versions.

Figure 14:
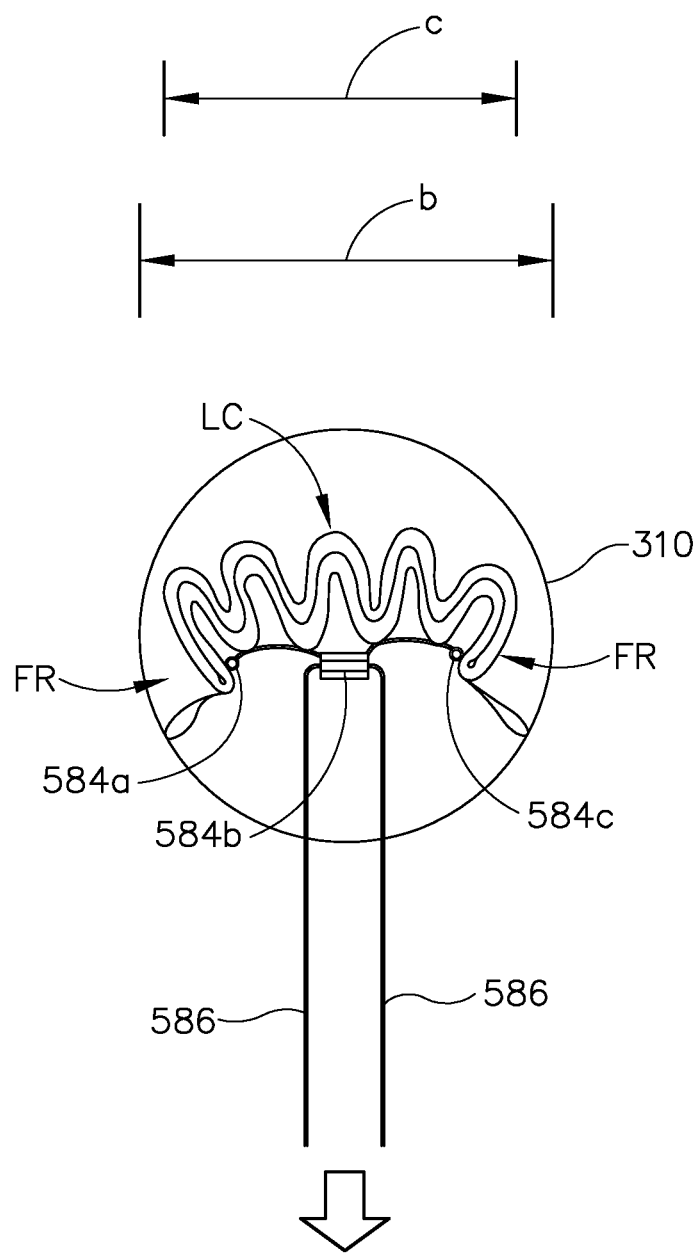
FIG. 14 depicts a top view of the portion of the gastrointestinal tract of FIG. 12 in a contracted configuration.

After staples (585), and suture assembly (580) have been applied to tissue as shown in FIG. 12, the operator may pull free ends (586) outwardly to shorten the length of the loop formed by suture (582). As the operator does this, suture (582) slides through suture retainers (584a, 584b, 584c) and along the space between the crowns of staples (585) and adjacent tissue. As the loop formed by suture (582) is shortened, the associated tissue is pulled inwardly in a pleated, bunched up configuration as shown in FIG. 14. As a result of this bunching up of tissue, the flap regions (FR) are drawn inwardly such that the tissue has an effective width (c). This effective width (c) is smaller than the diameter (b) of knife member (340), such that staples (585), suture assembly (580), and flap regions (FR) are all positioned within the cylindrical plane defined by knife member (340).

Figure 15A:
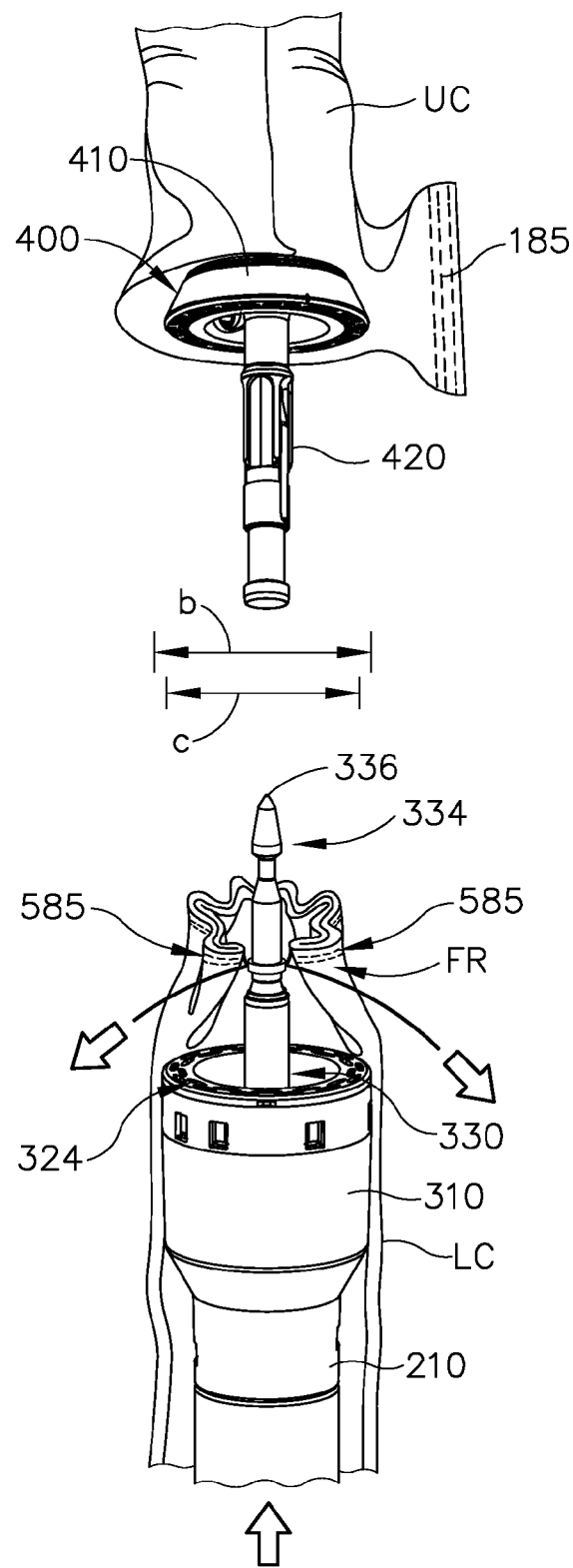
FIG. 15A depicts a schematic view of severed upper and lower portions of a patient's gastrointestinal tract, with an anvil of the circular stapler of FIG. 1 positioned in the upper portion of the gastrointestinal tract and a shaft of the circular stapler of FIG. 1 positioned in the lower portion of the gastrointestinal tract, with the staple cartridge of FIG. 11 having been used to staple and sever the gastrointestinal tract, and with the lower portion of the gastrointestinal tract in a contracted position, during a surgical procedure.
Figure 15B:
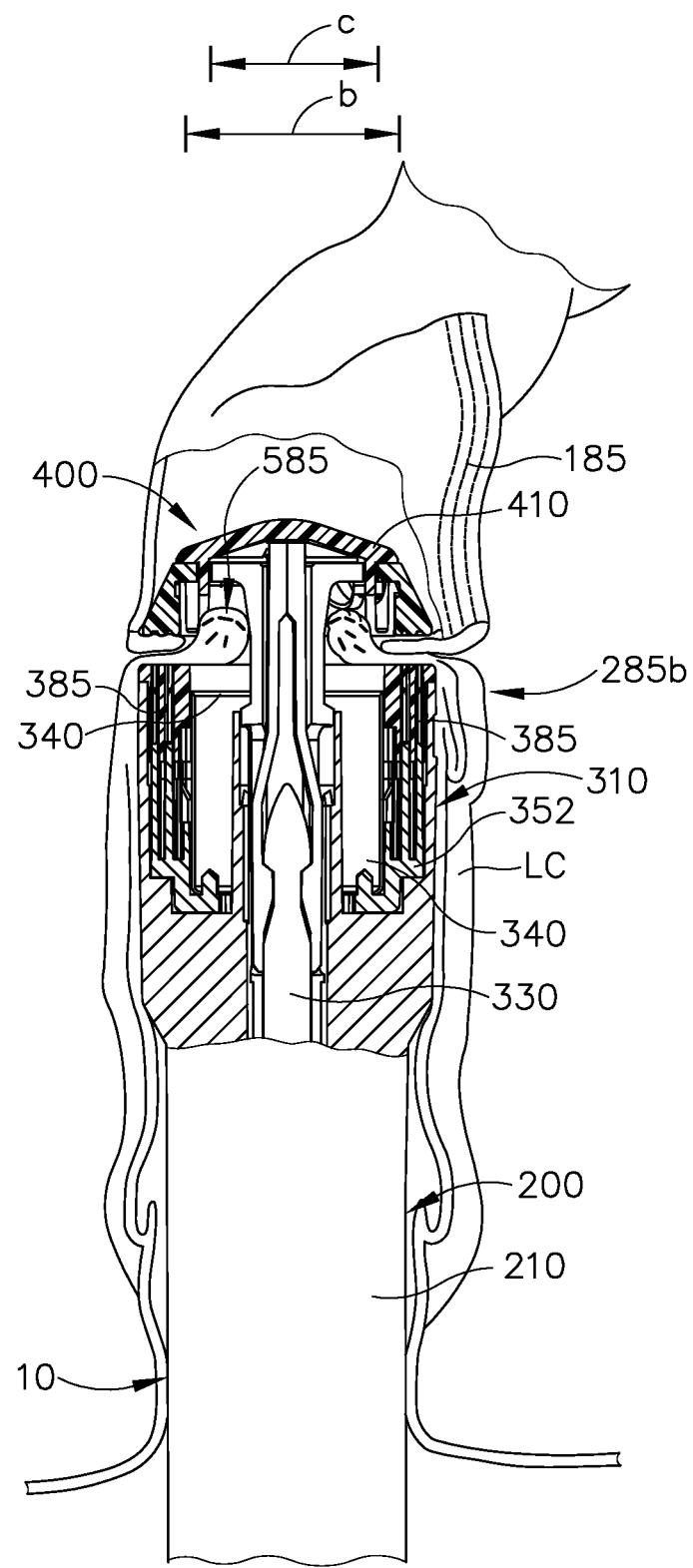
FIG. 15B depicts a schematic view of the gastrointestinal tract of FIG. 15A during another step of the surgical procedure of FIG. 15A, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.
Figure 15C:
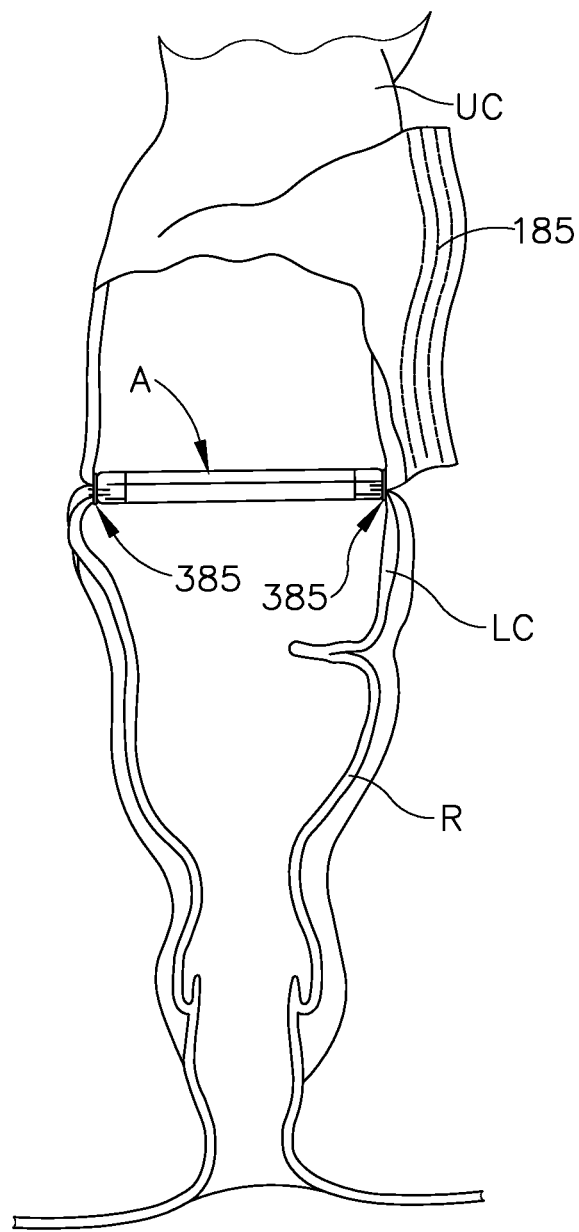
FIG. 15C depicts a schematic view of the gastrointestinal tract of FIG. 15A upon completion of the surgical procedure of FIG. 15A, with the upper and lower portions of the patient's gastrointestinal tract joined by staples deployed from the circular stapler of FIG. 1, providing an anastomosis between the upper and lower portions of the patient's gastrointestinal tract, with the anastomosis and adjacent regions of the gastrointestinal tract shown in cross-section.

FIGS. 15A-15C show steps of an anastomosis procedure similar to the procedure shown in FIGS. 7-10. Upper colon portion (UC) and lower colon portion (LC) are shown to have been severed and stapled in a similar manner to that shown in FIGS. 7-8. However, at least the lower colon portion (LC) has been severed and stapled utilizing staple cartridge (540). Lower colon portion (LC) therefore includes staples (585) and suture assembly (580) coupled thereto in the manner discussed above. As shown, a portion of shaft (210) and stapling head assembly (300) are inserted into the rectum (R) of the patient and into the lower portion (LC) of the colon (C). In the example shown, trocar (330) is inserted through the line of staples (585) such that trocar (330) is exposed out of lower colon portion (LC). Anvil (400) is shown to be positioned in the upper portion (UC) of the colon (C), with shank (420) extending through an opening of the upper colon portion (UC). As shown in FIG. 15A, ends (586) of suture (582) have been drawn away from trocar (330), resulting in the line of staples (585) and portion of the lower colon portion (LC) being drawn radially inwardly toward trocar (330). Thus, the tissue has an effective width (c) that is smaller than the diameter (b) of knife member (340), such that staples (585), suture assembly (580), and flap regions (FR) are all positioned within the cylindrical plane defined by knife member (340).

The operator then connects shank (420) to trocar (330) in the manner discussed above. Alternatively, the operator may draw the tissue of lower colon portion (LC) and the line of staples (585) radially inwardly after shank (420) and trocar (330) are coupled to one another. Referring to FIG. 15B, the operator may then draw anvil (400) toward stapling head assembly (300), in the manner described above (e.g., utilizing knob (130)), thus also drawing the upper colon portion (UC) toward the lower colon portion (LC). The operator may then retract trocar (330) until the tissue of the upper colon portion (UC) and the lower colon portion (LC) are compressed against the deck member (320) to achieve a desirable gap distance, as shown in FIG. 15B and discussed above.

The operator may then actuate trigger (150) to actuate stapling head assembly (300), resulting in the stapling and severing of tissue in a similar manner as shown in FIG. 9. Due to the staples (585), suture assembly (580), and flap regions (FR) all being positioned within the cylindrical plane defined by knife member (340), the combination of staples (585), suture assembly (580), and flap regions (FR) are all severed from the adjacent tissue. Thus, no staples (585) or components of suture assembly (580) are disposed in the tissue that remains at the resulting anastomosis (A) site as shown in FIG. 15C. Moreover, staples (585) do not impede the successful operation of circular stapler (10), and there are no flap regions (FR) extending outwardly from the anastomosis (A) site. The severed portion of tissue including staples (585) and suture assembly (580) may be removed by the operator via the patient's rectum.

Figure 13:
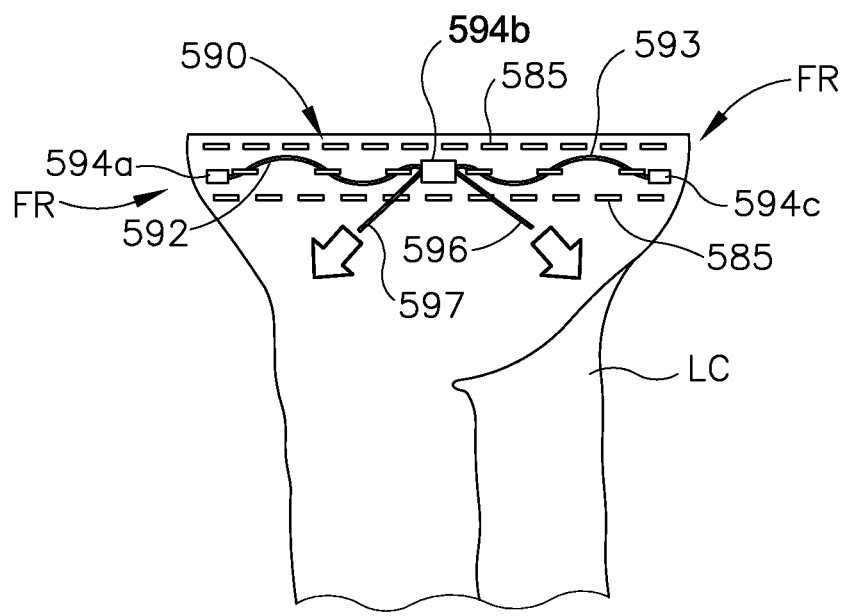
FIG. 13 depicts a side elevational view of a portion of the gastrointestinal tract after having been stapled and severed utilizing another exemplary alternative staple cartridge.

FIG. 13 shows an exemplary alternative suture assembly (590) secured to the tissue of a lower colon section (LC). It should be understood that suture assembly (590) may be readily incorporated into staple cartridge (540) in place of suture assembly (580). Suture assembly (590) of this example comprises a proximal suture retainer (594a), a middle suture retainer (594b), and a distal suture retainer (594c). Suture assembly (590) further comprises a first strand (592) and a second strand (593), which is separate from first strand (592). One end of first strand (592) is fixedly secured to proximal suture retainer (594a), while a free end (596) of first strand (592) slidably passes through middle suture retainer (594b). One end of second strand (593) is fixedly secured to distal suture retainer (594c), while a free end (597) of first strand (592) slidably passes through middle suture retainer (594b). Strands (592, 593) pass through middle suture retainer (594b) in a crisscross con-figuration. Strands (592, 593) are also arranged in a wave-like pattern and are positioned to be captured between crowns of staples (585) and adjacent tissue.

Middle suture retainer (594b) includes one-way passage features just like middle suture retainer (584b) described above. Thus, middle suture retainer (594b) allows free ends (596, 597) to be pulled outwardly to allow the length of strands (592, 593) to be shortened between middle suture retainer (594b) and corresponding suture retainers (594a, 594c); yet middle suture retainer (594b) prevents free ends (596, 597) from being pulled inwardly to increase the length of strands (592, 593) between middle suture retainer (594b) and corresponding suture retainers (594a, 594c). It should therefore be understood that suture assembly (590) may be deployed and operated just like suture assembly (580), to create a bunched-up tissue configuration to ensure that staples (585) and flap regions (FR) are located within the cylindrical plane defined by knife member (340).

B. Exemplary Alternative Staple Cartridge Including Suture and Staple Weave

Figure 16:
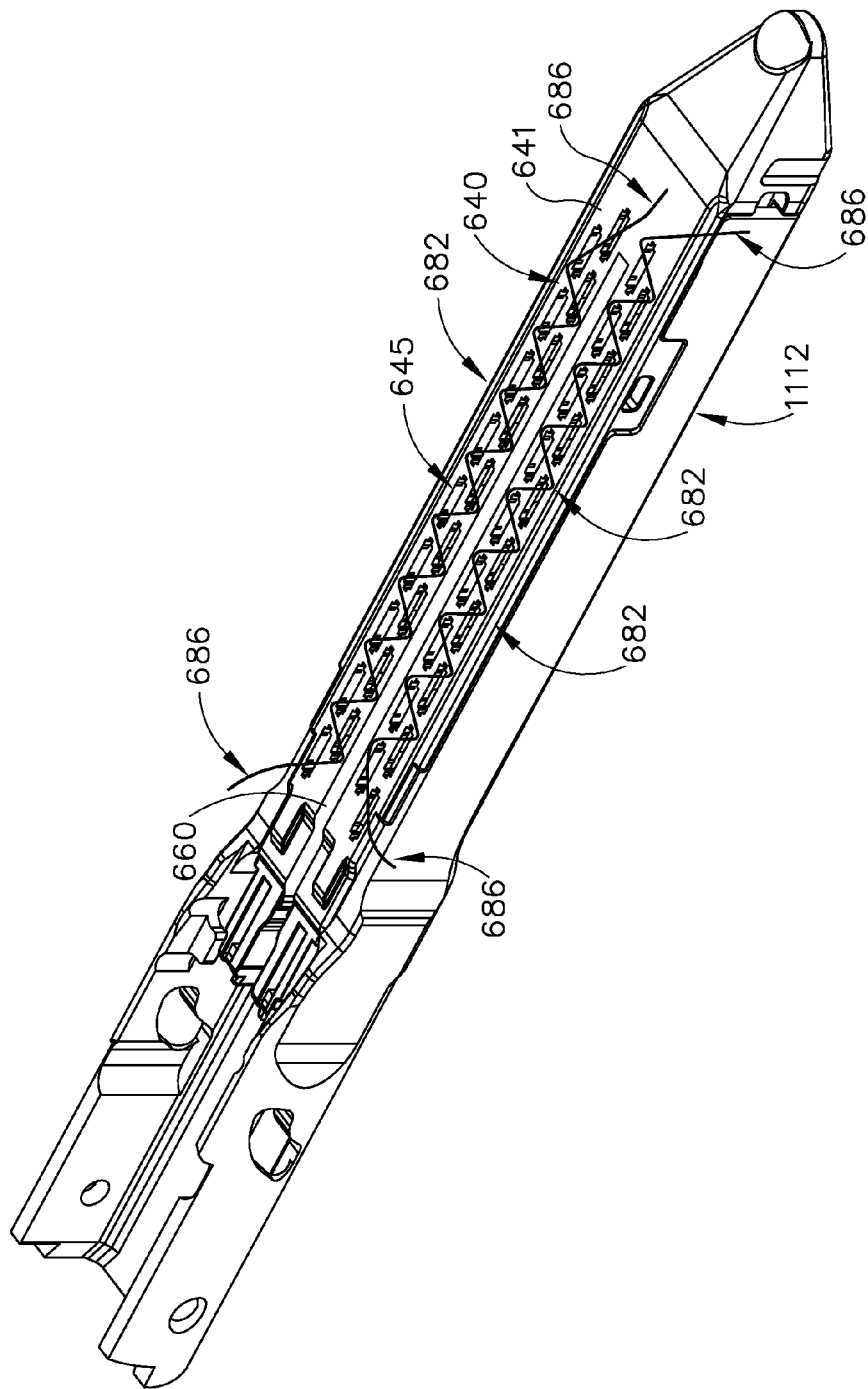
FIG. 16 depicts a perspective view of another exemplary alternative staple cartridge loaded into the lower jaw of the stapling device of FIG. 7, including a suture on a deck thereof, capable of being utilized in the procedure shown in FIGS. 7-10.

FIG. 16 shows an exemplary alternative staple cartridge (640) inserted in first jaw (1112) of end effector (1110). Staple cartridge (640) is substantially similar to staple cartridge (1140), except that staple cartridge (640) includes two rows of staple cavities (645) on each side of slot (660) of instead of three rows. Moreover, staple cartridge (640) includes a length of suture (682) on each side of slot (660). In the present example, suture (682) comprises any suitable monofilament or polyfilament material as will be apparent to persons skilled in the art in view of the teachings herein.

As shown in the present example, suture (682) extends in a zig-zag pattern from a proximal portion of cartridge deck (641) toward distal end of cartridge deck (641). Particularly, suture (682) on each side of slot (660) passes over each staple cavity (645) once. As shown, starting at the proximal-most cavity (645), each suture (682) extends in a repeating pattern distally and medially (toward slot (660)) such that the suture (682) extends over an adjacent cavity (645), and distally and laterally (away from slot (660)) back over the adjacent cavity (645). In the example shown, at least a portion of suture (682) is removably adhered to cartridge deck (641). However, in other examples, suture (582) may be affixed to cartridge deck (641) by other suitable methods. Other suitable configurations of suture (682) will be apparent to persons skilled in the art in view of the teachings herein.

Figure 17:
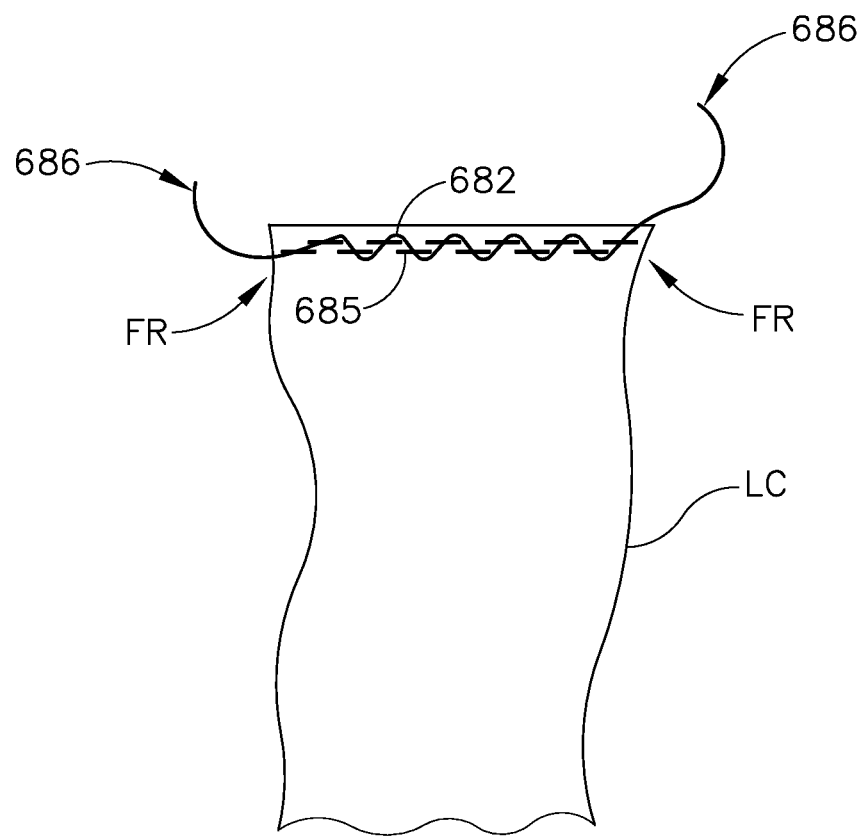
FIG. 17 depicts a side elevational view of portion of the gastrointestinal tract after having been stapled and severed utilizing the staple cartridge of FIG. 16.
Figure 18:
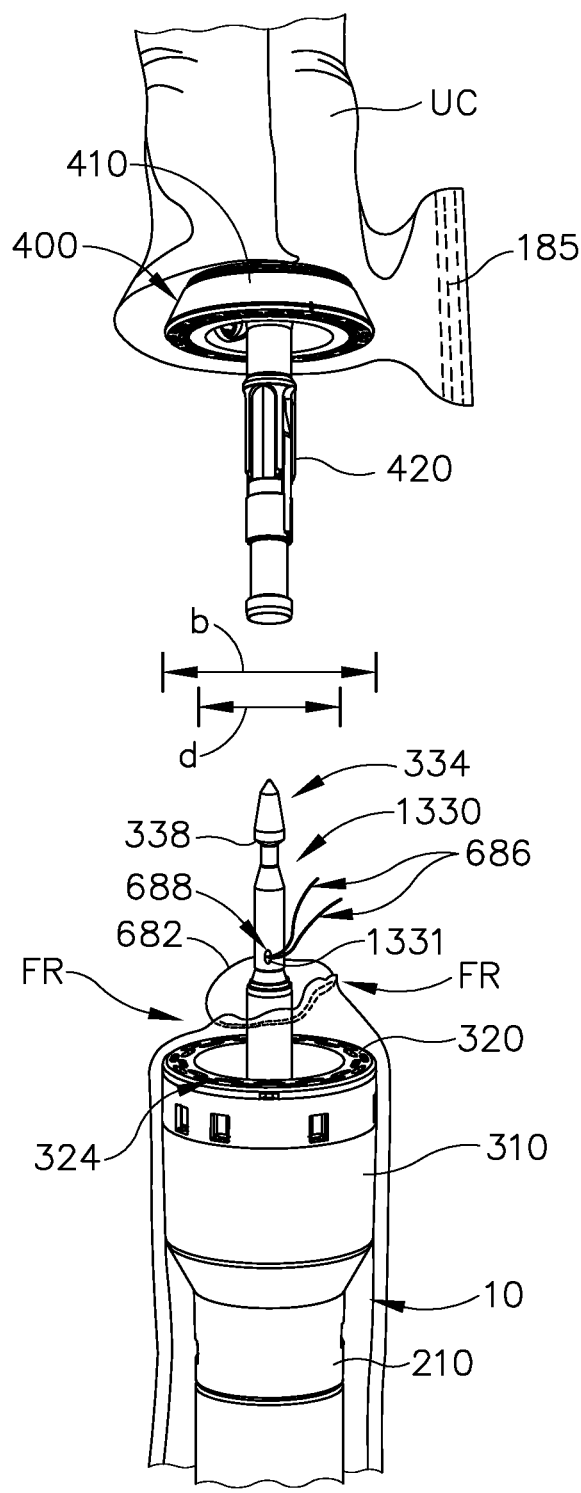
FIG. 18 depicts a schematic view of severed upper and lower portions of a patient's gastrointestinal tract, with an anvil of the circular stapler of FIG. 1 positioned in the upper portion of the gastrointestinal tract and a shaft of the circular stapler of FIG. 1 positioned in the lower portion of the gastrointestinal tract, with the staple cartridge of FIG. 16 having been used to staple and sever the gastrointestinal tract, and with the lower portion of the gastrointestinal tract in a contracted position, during a surgical procedure.

FIGS. 17 and 18 shows suture (682) and staples (685) coupled to a lower colon portion (LC) after an end effector (1100) that was loaded with staple cartridge (640) has been utilized to staple and sever a portion of lower colon portion (LC). In particular, FIG. 17 shows how suture (682) is secured to tissue by staples (685) in a zigzag arrangement. In particular, suture (682) extends along the full width of tissue, with free ends (686) of suture (682) extending outwardly from flap regions (FR). It should be understood that suture (682) is captured between the crowns of staples (685) and adjacent tissue; and that suture (682) may still slide between the crowns of staples (685) and adjacent tissue. Suture (682) is thus secured to the tissue via staples (682) in a manner similar to a purse string weave.

FIG. 18 shows a step of an anastomosis procedure similar to the steps shown in FIGS. 8 and 15A. Particularly, upper colon portion (UC) and lower colon portion (LC) have been severed and stapled in a similar manner to that shown in FIGS. 7-8 and 15A-B. However, at least the lower colon portion (LC) has been severed and stapled utilizing staple cartridge (640). Lower colon portion therefore includes staples (685) and suture (682) coupled thereto in the manner discussed above. As shown, a portion of shaft (210) and stapling head assembly (300) are inserted into the rectum (R) of the patient and into the lower portion of the colon (C). As also shown, the circular stapler (10) of this example includes a modified trocar (1330) that is substantially identical to trocar (330), except that trocar (1330) includes a lateral aperture (1331) formed therein. In the example shown, trocar (1330) is inserted through the line of staples (685) such that trocar (1330) is exposed out of lower colon portion (LC). Trocar (1330) and lower colon portion (LC) are further positioned in relation to each other such that lateral aperture (1331) is exposed relative to lower colon portion (LC).

Anvil (400) is shown to be positioned in the upper portion (UC) of the colon (C), with shank (420) extending through an opening of the upper colon portion (UC). As shown, ends (686) of suture (682) are pulled to cause the stapled tissue to bunch up, such that flap regions (FR) are brought toward each other and such that the tissue defines an effective width (d) that is smaller than the diameter (b) of knife member (340). Thus, staples (685), suture (682), and flap regions (FR) are all positioned within the cylindrical plane defined by knife member (340). The operator then pulls ends (686) of suture (682) through lateral aperture (1331) of trocar (1330), and secures ends (686) relative to trocar (1330) by tying a knot (688). Knot (688) thus cooperates with trocar (1330) to hold the tissue in the bunched up configuration, thereby maintaining the effective width (d). Other suitable ways in which suture (682) may be secured relative to trocar (1330) will be apparent to persons skilled in the art in view of the teachings herein.

The operator then connects shank (420) to trocar (1330) in the manner discussed above. Alternatively, the user may draw the tissue of lower colon portion and the line of staples (585) radially inwardly and couple suture (682) relative to trocar (1330) after shank (420) and trocar (1330) are coupled to one another. The operator may then draw anvil (400) toward stapling head assembly (300), in the manner described above (e.g., utilizing knob (130)), thus also drawing the upper colon portion (UC) toward the lower colon portion (LC). The operator may then retract trocar (1330) until the tissue of the upper colon portion (UC) and the lower colon portion (LC) are compressed against the deck member (320) to achieve a desirable gap distance, in a similar manner as shown in FIG. 15B.

The operator may then actuate trigger (150) to actuate stapling head assembly (300), resulting in the stapling and severing of tissue in a similar manner as shown in FIG. 9. Due to the staples (685), suture (682), and flap regions (FR) all being positioned within the cylindrical plane defined by knife member (340), the combination of staples (685), suture (682), and flap regions (FR) are all severed from the adjacent tissue. Thus, no staples (685) or suture (682) are disposed in the tissue that remains at the resulting anastomosis site. Moreover, staples (685) do not impede the successful operation of circular stapler (10), and there are no flap regions (FR) extending outwardly from the anastomosis site. The severed portion of tissue including staples (685) and suture (682) may be removed by the operator via the patient's rectum.

Figure 19:
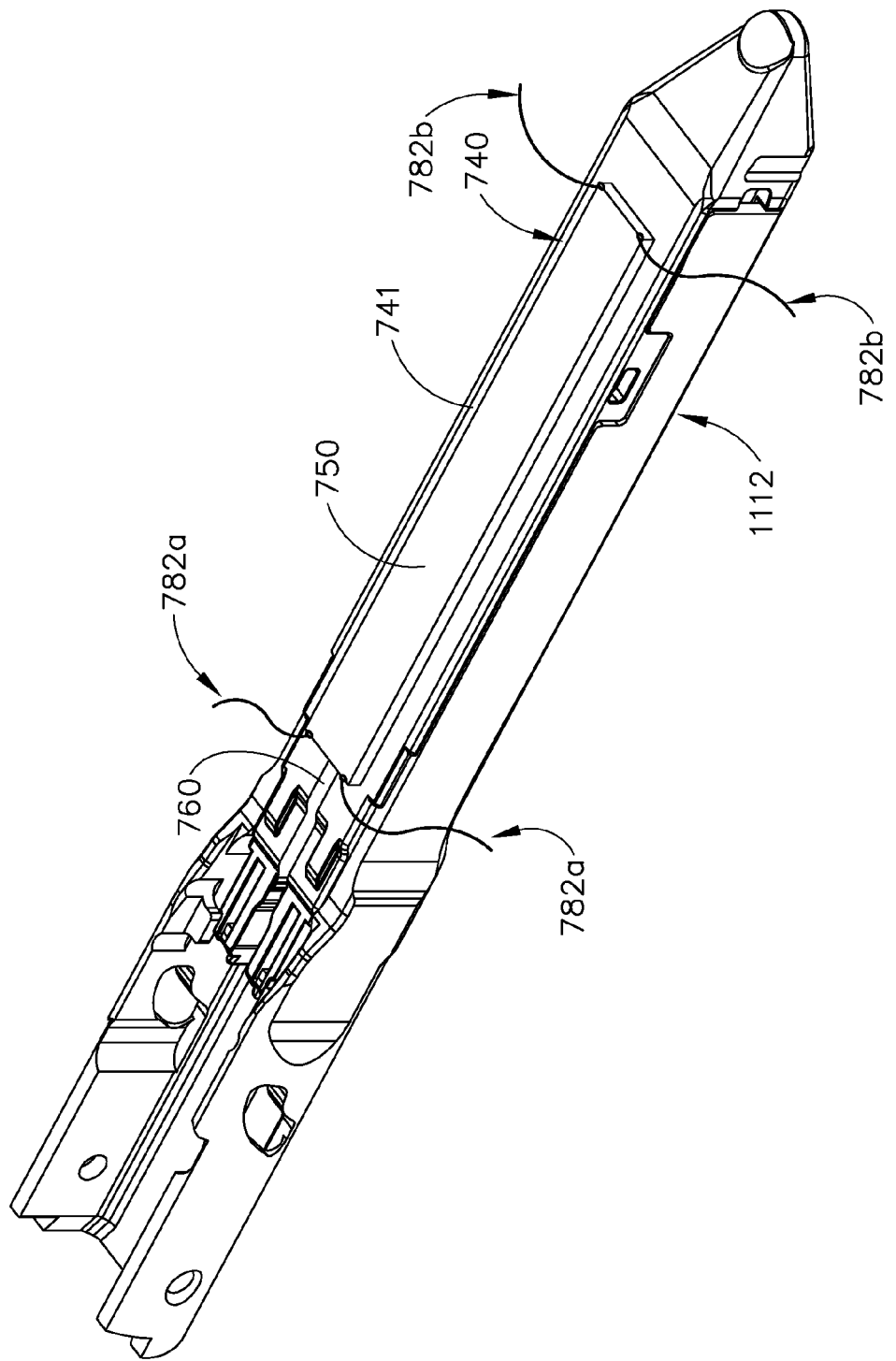
FIG. 19 a perspective view of another exemplary alternative staple cartridge loaded into the lower jaw of the stapling device of FIG. 7, including an buttress on a deck thereof, capable of being utilized in the procedure shown in FIGS. 7-10.

C. Exemplary Alternative Staple Cartridge Including Buttress with Integral Sutures for Securing Stapled Tissue to Trocar FIG. 19 shows an exemplary alternative staple cartridge (740) inserted in first jaw (1112) of end effector (1110). Staple cartridge (740) is substantially similar to staple cartridge (1140), except that staple cartridge (740) includes two rows of staple cavities (not shown) on each side of a slot (760) of instead of three rows. Moreover, staple cartridge (740) includes a buttress (750) that is removably secured to a deck (741) of cartridge (740). Various suitable forms that the body of buttress (750) may take will be apparent to those of ordinary skill in the art in view of the teachings herein. By way of example only, the body of buttress (750) may be formed by a mesh of woven material that is provided in the form of a thin sheet.

Buttress (750) includes an integral pair of proximal sutures (782a) and an integral pair of distal sutures (782b). Sutures (782a, 782b) are formed as strands having free ends that may be manipulated in the manner described below. In the example shown, buttress (750) is removably adhered to deck (741), but in other examples buttress (750) may be associated with or coupled to cartridge (740) in a different manner (e.g., via clips, via hook and loop fasteners, etc.). When an end effector (1110) that incorporates staple cartridge (740) is actuated, buttress (750) will be severed along slot (760) and stapled onto tissue along with staples (785), as shown best in FIG. 20A.

Figure 20A:
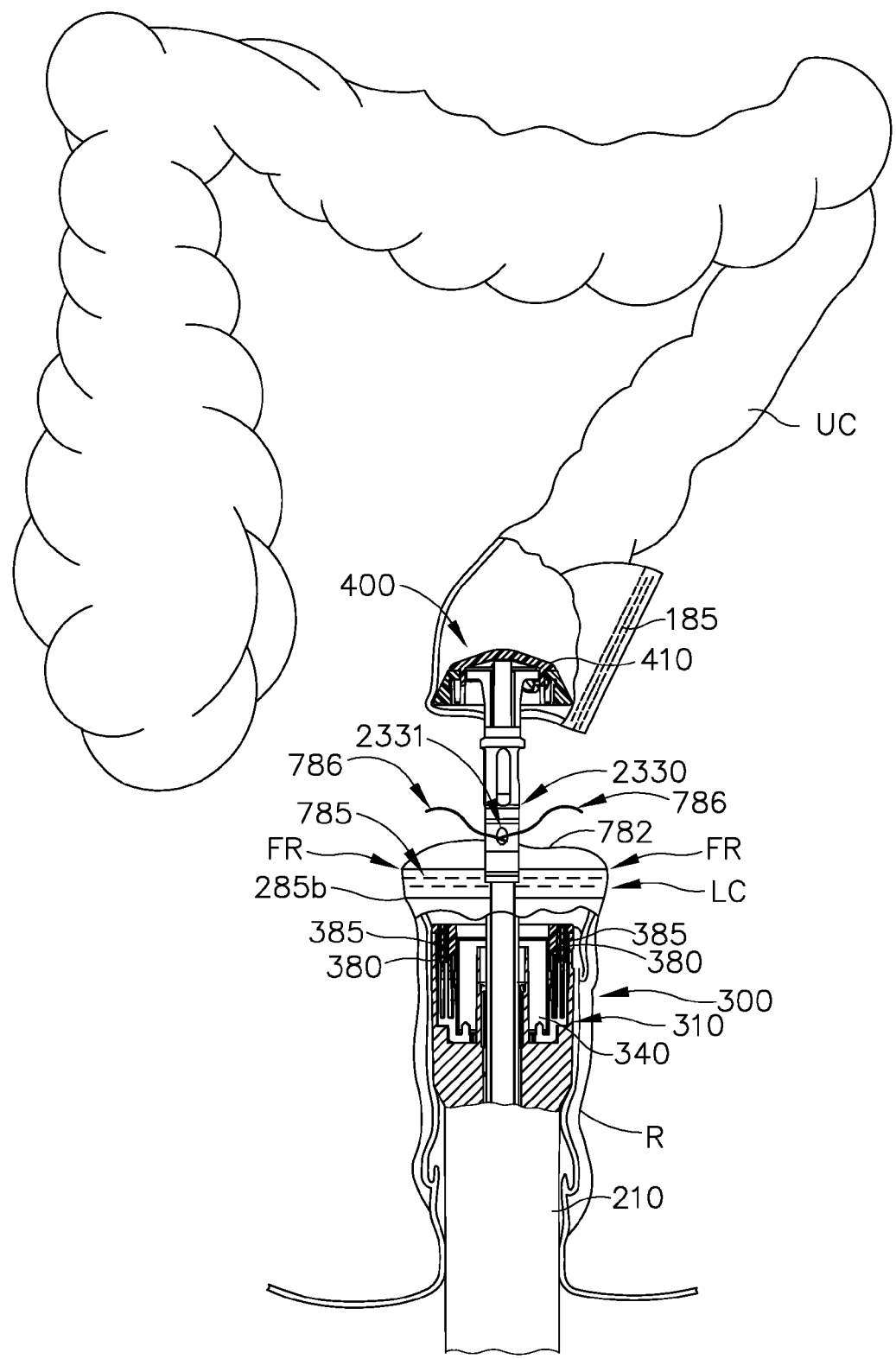
FIG. 20A depicts a schematic view of the gastrointestinal tract of FIG. 7 during a surgical procedure, showing the anvil of FIG. 3 positioned in the upper portion of the gastrointestinal tract and the stapling head assembly of FIG. 4 positioned in the lower portion of the gastrointestinal tract, with the staple cartridge of FIG. 19 having been used to staple and sever the gastrointestinal tract, showing the portion of the gastrointestinal tract in a contracted position, with the anvil and the stapling head assembly and adjacent regions of the gastrointestinal tract shown in cross-section.
Figure 20B:
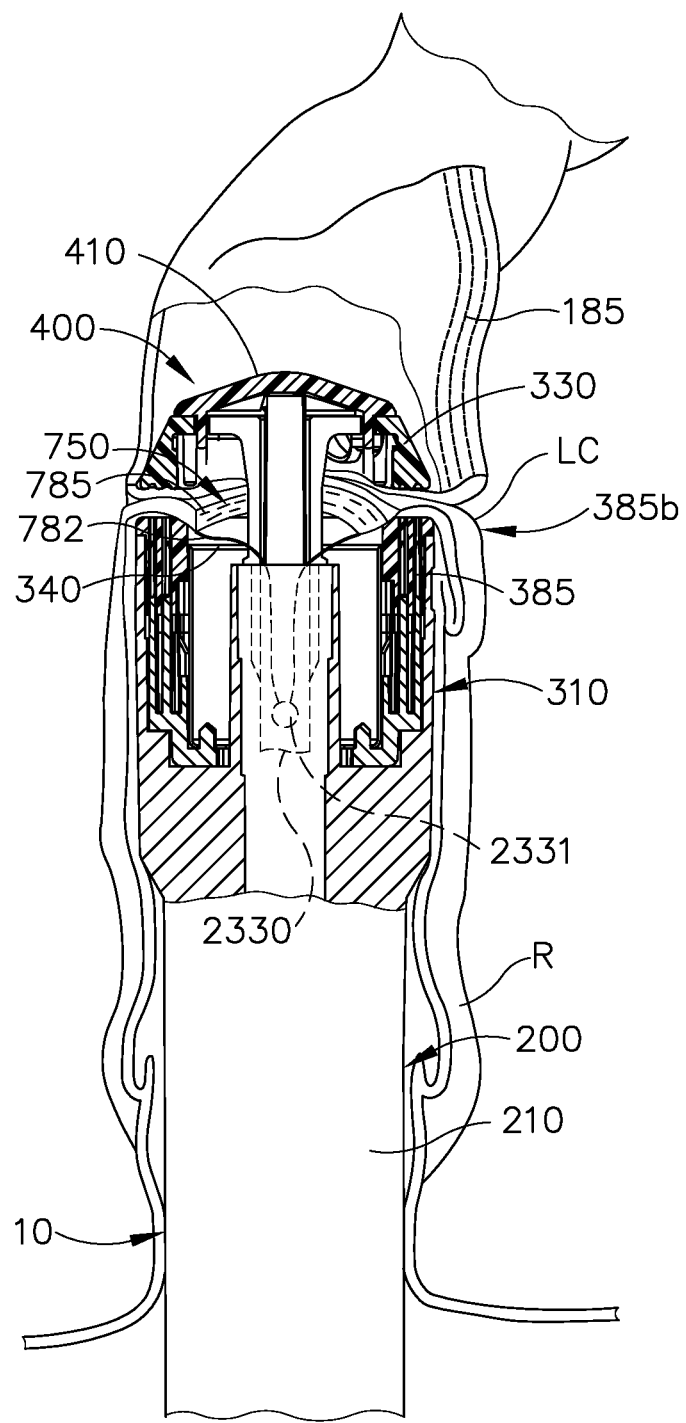
FIG. 20B depicts a schematic view of the gastrointestinal tract of FIG. 20A during another step of the surgical procedure of FIG. 20A, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.

FIGS. 20A-20B show certain steps of an anastomosis procedure that is substantially similar to the procedure shown in FIGS. 7-10 and 15A-C. Particularly, at the stage shown in FIG. 20A, upper colon portion (UC) and lower colon portion (LC) have been severed and stapled in a manner similar to that shown in FIGS. 7-8, 15A, and 18. However, at least the lower colon portion (LC) has been severed and stapled utilizing staple cartridge (740) in this example. Lower colon portion (LC) therefore includes staples (785) and buttress (750) coupled thereto in the manner discussed above. As shown, a portion of shaft (210) and stapling head assembly (300) are inserted into the rectum (R) of the patient and into the lower portion (LC) of the colon (C). As also shown, circular stapler (10) of this example includes a modified trocar (2330) that is substantially identical to trocar (330), except that trocar (2330) of this example includes a lateral aperture (2331). The relative placement of aperture (2331) on trocar (2330) is more proximal than the placement of aperture (1331) on trocar (1330), which is discussed in further detail below. In the example shown, trocar (2330) is inserted through the line of staples (785) such that trocar (2330) is exposed out of lower colon portion (LC). Trocar (2330) and lower colon portion (LC) are further positioned in relation to each other such that lateral aperture (2331) is exposed relative to lower colon portion (LC).

Anvil (400) is shown to be positioned in the upper portion (UC) of the colon (C), with shank (420) extending through an opening of the upper colon portion (UC). The operator then connects shank (420) to trocar (2330) in a similar manner as discussed above with respect to shank (420) and trocar (330). Before or after the shank (420) and trocar (2330) are coupled to one another, the operator may couple the distal and proximal sutures (782a, 782b) to trocar (2330) via aperture (2331). In the example shown, aperture (2331) is in an accessible distal position (FIG. 20A) prior to the anvil (400) being drawn toward stapling head assembly (300); and retractable to a less accessible, proximal position (FIG. 20B). Due to the coupling between sutures (782a, 782b), as the operator draws anvil (400) toward stapling head assembly (300) to the position shown in FIG. 20B (e.g., utilizing knob (130)), sutures (782a, 782b) are drawn proximally. As sutures (782a, 782b) are drawn proximally, sutures (782a, 782b) draw the respective proximal and distal portions of buttress (750) proximally and radially inwardly relative to stapling head assembly (300). This results in staples (785), buttress (750), and the associated flap regions (FR) being positioned within the cylindrical plane defined by knife member (340), as shown in FIG. 20B.

The operator may then actuate trigger (150) to actuate stapling head assembly (300), resulting in the stapling and severing of tissue in a similar manner as shown in FIG. 9. Due to staples (785), buttress (750), and the associated flap regions (FR) all being positioned within the cylindrical plane defined by knife member (340), the combination of staples (785), buttress (750), and the associated flap regions (FR) are all severed from the adjacent tissue. Thus, no staples (785) are disposed in the tissue that remains at the resulting anastomosis site. Moreover, staples (785) do not impede the successful operation of circular stapler (10), and there are no flap regions (FR) extending outwardly from the anastomosis site. The severed portion of tissue including staples (785) and buttress (750) may be removed by the operator via the patient's rectum.

Figure 21:
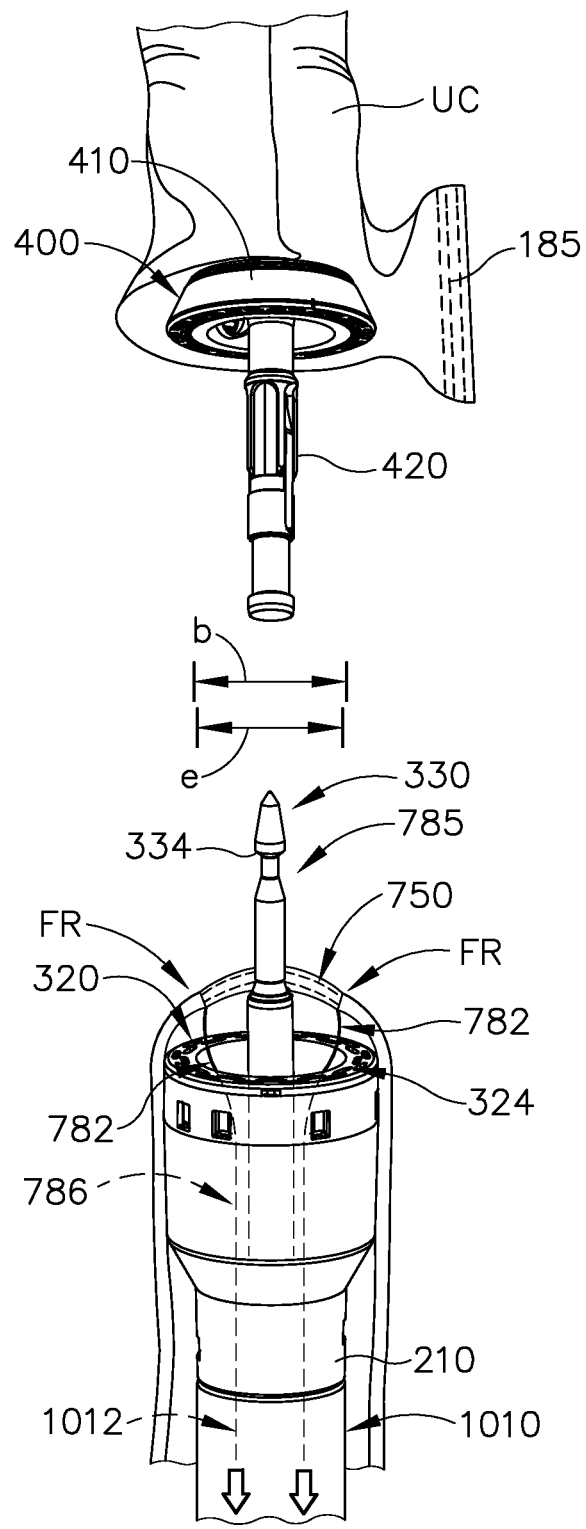
FIG. 21 depicts a schematic view of severed upper and lower portions of a patient's gastrointestinal tract, with an anvil of the circular stapler of FIG. 1 positioned in the upper portion of the gastrointestinal tract and a shaft of the circular stapler of FIG. 1 positioned in the lower portion of the gastrointestinal tract, with suture strands being pulled through the shaft assembly of the circular stapler to contract the lower portion of the gastrointestinal tract during a surgical procedure

It should be understood that the foregoing example provides cinching of tissue, and thus drawing-in of flap regions (FR) based on the proximal retraction of anvil (400) toward stapling head assembly (300). As another merely illustrative variation, as shown in FIG. 21, sutures (782) may be fed through stapling head assembly (300) and may be pulled proximally by the operator. In particular, FIG. 21 shows an alternative circular stapler (1010) that includes a lumen (1012) into which sutures (782a, 782b) may be directed. Lumen (1012) is communication with an opening (not shown) that provides the operator with access to sutures (782a, 782b) and thereby enables the operator to pull proximally on sutures (782a, 782b) in order to draw the lines of staples (785) and the lower colon portion (LC) radially inwardly toward trocar (330). As shown, sutures (782a, 782b) are pulled in a manner sufficient to cause the stapled tissue to bunch up, such that flap regions (FR) are brought toward each other and such that the tissue defines an effective width (e) that is smaller than the diameter (b) of knife member (340). Thus, staples (785), buttress (750), and the associated flap regions (FR) are all positioned within the cylindrical plane defined by knife member (340) as described above. Other suitable ways in which sutures (782a, 782b) may be manipulated to draw staples (785), buttress (750), and the associated flap regions (FR) within the cylindrical plane defined by knife member (340) will be apparent to those of ordinary skill in the art in view of the teachings herein.

Figure 22:
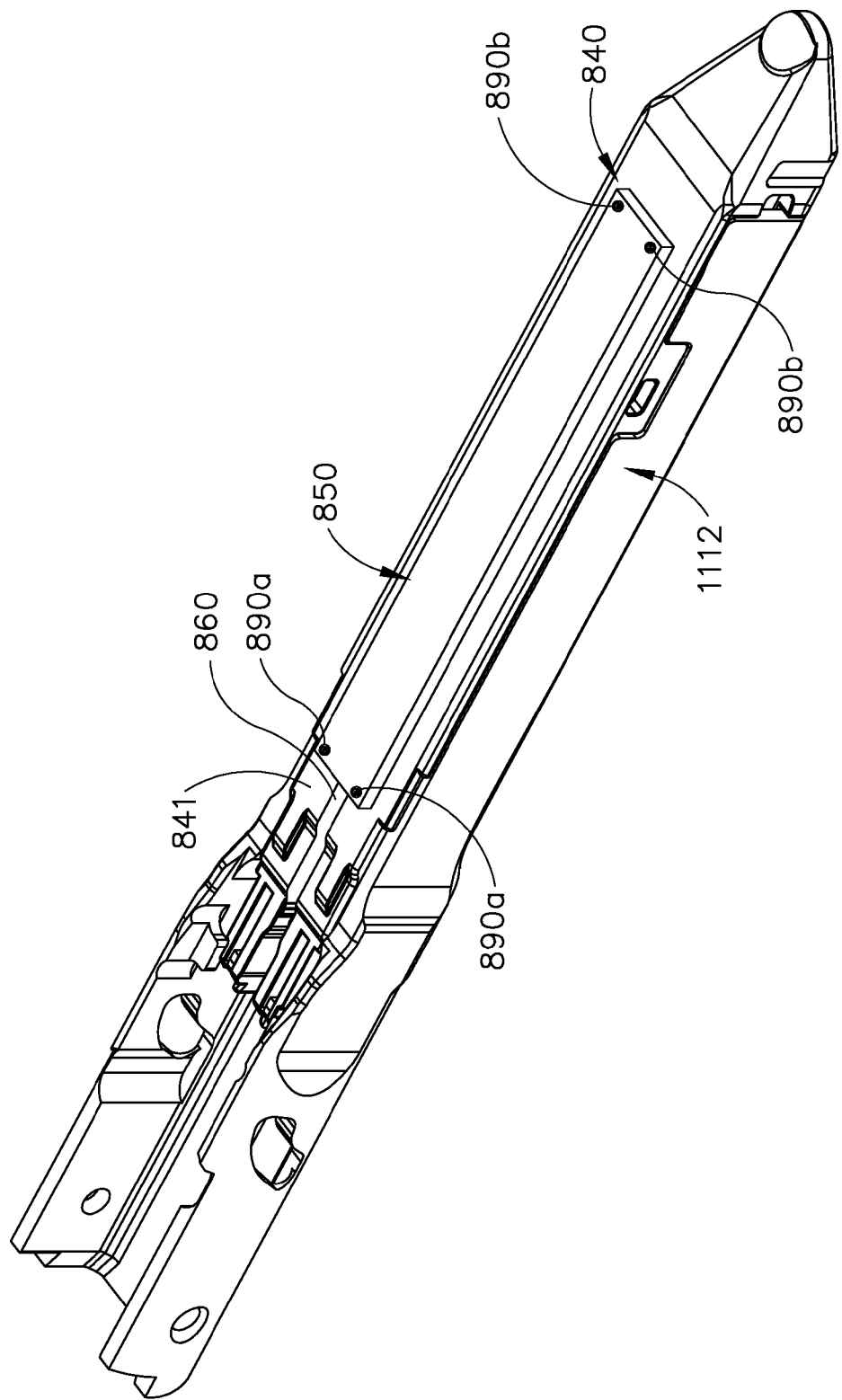
FIG. 22 depicts a perspective view of another exemplary alternative staple cartridge loaded into the lower jaw of the stapling device of FIG. 7, including an buttress on a deck thereof, capable of being utilized in the procedure shown in FIGS. 7-10.

D. Exemplary Alternative Staple Cartridge Including Buttress with Integral Grommets for Securing Stapled Tissue to Trocar FIG. 22 shows another exemplary alternative staple cartridge (840) inserted in first jaw (1112) of end effector (1110). Staple cartridge (840) is substantially similar to staple cartridge (1140), except that staple cartridge (840) includes two rows of staple cavities (not shown) on each side of a slot (860) of instead of three rows. Moreover, staple cartridge (840) includes a buttress (850) that is removably secured to a deck (841) of cartridge (840). Various suitable forms that the body of buttress (850) may take will be apparent to those of ordinary skill in the art in view of the teachings herein. By way of example only, the body of buttress (850) may be formed by a mesh of woven material that is provided in the form of a thin sheet.

Buttress (850) includes an integral pair of proximal grommets (890a) and an integral pair of distal grommets (890b). Grommets (890a, 890b) are formed as reinforced openings through the body of buttress (850). In the example shown, buttress (850) is removably adhered to deck (841), but in other examples buttress (750) may be associated with or coupled to cartridge (840) in a different manner (e.g., via clips, via hook and loop fasteners, etc.). When an end effector (1110) that incorporates staple cartridge (840) is actuated, buttress (850) will be severed along slot (860) and stapled onto tissue along with staples (885), as shown best in FIG. 23.

Figure 23:
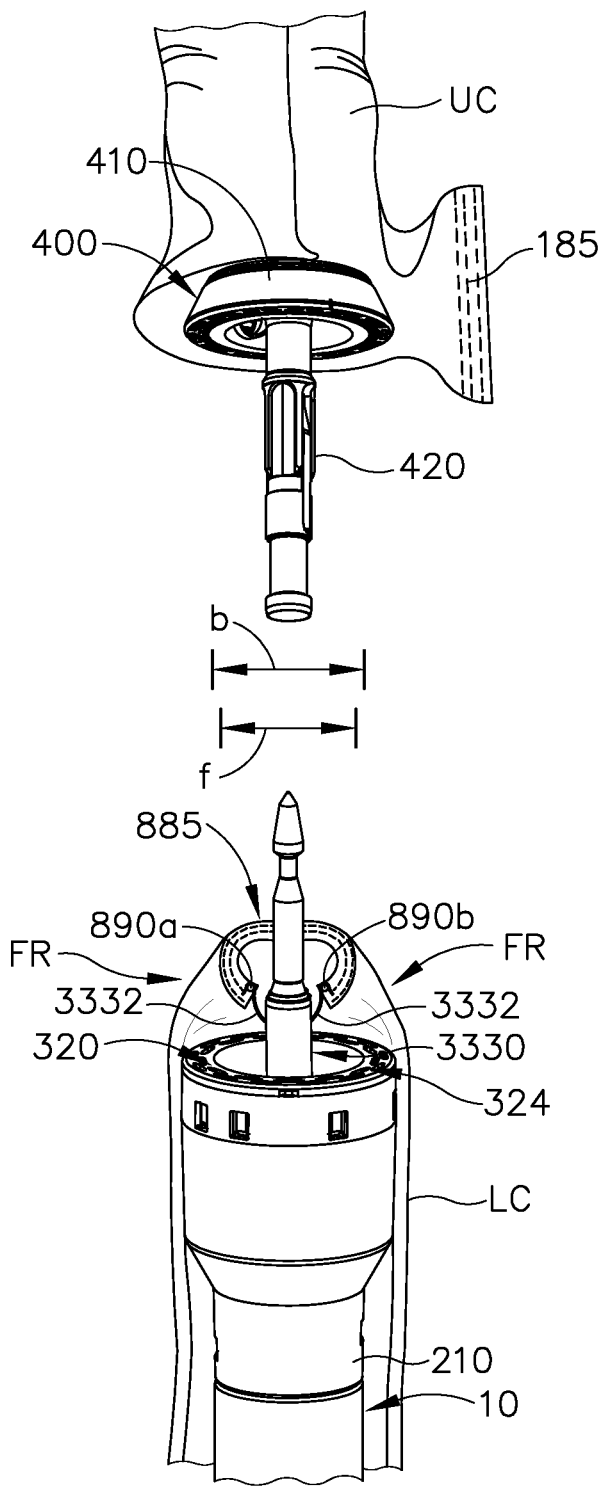
FIG. 23 depicts a schematic view of severed upper and lower portions of a patient's gastrointestinal tract, with an anvil of the circular stapler of FIG. 1 positioned in the upper portion of the gastrointestinal tract and a shaft of the circular stapler of FIG. 1 positioned in the lower portion of the gastrointestinal tract, with the staple cartridge of FIG. 22 having been used to staple and sever the gastrointestinal tract, and with the lower portion of the gastrointestinal tract in a contracted position, during a surgical procedure.

FIG. 23 shows a portion of an anastomosis procedure that is substantially similar to the procedure shown in FIGS. 7-10 and 15A-C. Particularly, upper colon portion (UC) and lower colon portion (LC) have been severed and stapled in a similar manner to that shown in FIGS. 7-8, 15A, 18, 20A, and 21. However, at least the lower colon portion (LC) has been severed and stapled utilizing staple cartridge (840). Lower colon portion (LC) therefore includes staples (885) and buttress (850) coupled thereto in the manner discussed above. As shown, a portion of shaft (210) and stapling head assembly (300) are inserted into the rectum (R) of the patient and into the lower portion of the colon (C). As also shown, circular stapler (10) of this example includes a modified trocar (3330) that is substantially identical to trocar (330), except that trocar (2330) of this example includes an opposing set of outwardly projecting hooks (3332). In the example shown, trocar (2330) is inserted through the line of staples (785) such that trocar (3330) is exposed out of lower colon portion (LC). Trocar (3330) and lower colon portion (LC) are further positioned in relation to each other such that hooks (3332) are exposed relative to lower colon portion (LC).

Anvil (400) is shown to be positioned in the upper portion (UC) of the colon (C), with shank (420) extending through an opening of the upper colon portion (UC). The operator then connects shank (420) to trocar (2330) in a similar manner as discussed above with respect to shank (420) and trocar (330). Before or after the shank (420) and trocar (2330) are coupled to one another, the operator may engage the distal and proximal grommets (890a, 890b) with respective hooks (3332) of trocar (3330). Alternatively, grommets (890a, 890b) may be engaged with only one hook (3332) of trocar (3330). As shown in FIG. 23, line of staples (885) and portion of the lower colon portion (LC) are drawn radially inwardly toward trocar (3330) due to coupling between grommets (890a, 890b) and hooks (3332). As the operator retracts anvil (400) toward stapling head assembly (300) to clamp tissue, the proximally retracting trocar (3300) draws the tissue at the severed end of lower colon section (LC) inwardly. In particular, grommets (890a, 890b) are pulled in a manner sufficient to cause the stapled tissue to bunch up, such that flap regions (FR) are brought toward each other and such that the tissue defines an effective width (f) that is smaller than the diameter (b) of knife member (340). Thus, staples (885), buttress (850), and the associated flap regions (FR) are all positioned within the cylindrical plane defined by knife member (340) as described above. Other suitable ways in which grommets (890a, 890b) may be manipulated to draw staples (885), buttress (850), and the associated flap regions (FR) within the cylindrical plane defined by knife member (340) will be apparent to those of ordinary skill in the art in view of the teachings herein.

After the operator has drawn in the tissue at the severed end of lower colon section (LC), and after the operator has clamped tissue with an appropriate gap between anvil (400) and stapling head assembly (300), the operator may actuate trigger (150) to actuate stapling head assembly (300), resulting in the stapling and severing of tissue in a similar manner as shown in FIGS. 9 and 15C. As with the example shown in FIGS. 15A-C, due to staples (885), buttress (850), and the associated flap regions (FR) all being positioned within the cylindrical plane defined by knife member (340), the combination of staples (885), buttress (850), and the associated flap regions (FR) are all severed from the adjacent tissue. Thus, no staples (885) are disposed in the tissue that remains at the resulting anastomosis site. Moreover, staples (885) do not impede the successful operation of circular stapler (10), and there are no flap regions (FR) extending outwardly from the anastomosis site. The severed portion of tissue including staples (885) and buttress (850) may be removed by the operator via the patient's rectum.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising a staple cartridge, wherein the staple cartridge comprises: (i) a plurality of staples, (ii) a deck, wherein the deck defines a plurality of openings, wherein each opening of the plurality of openings is associated with a corresponding staple of the plurality of staples, such that each staple is configured to pass through a corresponding opening of the plurality of openings, and (ii) a cinching feature positioned on the deck, wherein the cinching feature is configured to be coupled to tissue in response to actuation of the staple cartridge, wherein the cinching feature is configured to cinch a portion of stapled tissue toward an inwardly cinched position.

Example 2

The apparatus of Example 1, wherein the cinching feature comprises at least one suture positioned over at least some of the staple openings.

Example 3

The apparatus of Example 2, wherein the at least one suture extends over each of the staple openings.

Example 4

The apparatus of any one or more of Examples 2 through 3, wherein the cinching feature further comprises a plurality of suture retainers operably coupled to the suture.

Example 5

The apparatus of any one or more of Examples 2 through 4, wherein the deck comprises a slot, wherein the at least one suture comprises a first suture positioned on a first side of the slot and a second suture positioned on a second side of the slot.

Example 6

The apparatus of any one or more of Examples 1 through 5, wherein the cinching feature is adhered to the deck.

Example 7

The apparatus of any one or more of Examples 1 through 6, wherein the cinching feature comprises a buttress disposed on the deck.

Example 8

The apparatus of Example 7, wherein the buttress comprises at least one suture coupled thereto.

Example 9

The apparatus of any one or more of Examples 7 through 8, wherein the buttress comprises a proximal end and a distal end, wherein the proximal end includes a pair of opposing sutures and the distal end includes a pair of opposing sutures.

Example 10

The apparatus of any one or more of Examples 7 through 9, wherein the buttress is configured to be severed in response to activation of the severing and stapling assembly.

Example 11

The apparatus of any one or more of Examples 7 through 10, wherein the buttress comprises at least one aperture.

Example 12

The apparatus of any one or more of Examples 7 through 11, wherein the buttress comprises a proximal end and a distal end, wherein the proximal end includes a pair of opposing apertures and the distal end includes a pair of opposing apertures.

Example 13

The apparatus of any one or more of Examples 1 through 12, further comprising a circular stapler, wherein the circular stapler comprises: (i) an anvil, and (ii) a stapling head assembly, wherein the stapling head assembly comprises: (A) a rod configured to engage the anvil, (B) a knife member configured to form a circular cut line in tissue, and (C) a staple driver, wherein the anvil and stapling head assembly are configured to cooperate to clamp and staple tissue; wherein the cinching feature is configured to be coupled to the rod when the circular stapler is associated with tissue stapled and severed by the apparatus.

Example 14

The apparatus of Example 13, wherein the rod includes an aperture configured to receive a portion of the cinching feature.

Example 15

The apparatus of any one or more of Examples 13 through 14, wherein the rod includes at least one hook configured to engage a portion of the cinching feature Example 16

A method of operating on tissue using a circular stapler, wherein the circular stapler comprises an anvil and a stapling head assembly, wherein the stapling head assembly comprises a rod, a knife member, and a staple driver, wherein the knife member defines a circular cut line, wherein the anvil and stapling head assembly are configured to cooperate to clamp and staple tissue, wherein the method comprises: (a) severing and stapling a first portion of anatomical structure using a non-circular stapler, thereby leaving a plurality of staples on a severed end portion of the first portion of an anatomical structure; (b) inserting the anvil of the circular stapler into a second portion of the anatomical structure; (c) inserting the stapling head assembly into the first portion of the anatomical structure until at least a portion of the rod extends past the severed end portion of the first portion of the anatomical structure; (d) drawing the severed end portion inwardly toward the rod such that the plurality of staples on the severed end portion lie inward of the circular cut line of the knife member; (e) coupling the rod and the anvil; (f) clamping the first and second portions of the anatomical structure together; and (g) driving the knife member toward the anvil, thereby severing the severed end portion and the staples from the first portion of the anatomical structure and at least part of the second portion of the anatomical structure; and (h) stapling the first and second portions of the anatomical structure together.

Example 17

The apparatus of Example 16, wherein the first portion of the anatomical structure comprises a first portion of a colon, wherein the second portion of the anatomical structure comprises a second portion of the colon.

Example 18

A method of forming an anastomosis between two portions of a colon using a circular stapler, wherein the circular stapler comprises an anvil and a stapling head assembly, wherein the stapling head assembly comprises a rod, a knife member, and a staple driver, wherein the knife member defines a circular cut line, wherein the anvil and stapling head assembly are configured to cooperate to clamp and staple tissue, wherein the method comprises: (a) severing and stapling a first portion of the colon using a non-circular stapler, thereby leaving a first plurality of staples on a first severed end portion of the first portion of the colon; (b) severing and stapling a second portion of the colon using a non-circular stapler, thereby leaving a second plurality of staples on a second severed end portion of the second portion of the colon; (c) inserting the anvil of the circular stapler into the second portion of the patient's colon; (d) inserting the stapling head assembly into the first portion of the colon until at least a portion of the rod extends past the severed end portion of the first anatomical structure; (e) drawing the first severed end portion inwardly toward the rod such that the first plurality of staples and the first severed end portion lie radially inwardly of the circular cut line of the knife member; (f) driving the knife member toward the anvil, thereby severing the first severed end portion and the first plurality of staples from the first portion of the patient's colon and at least part of the second portion of the patient's colon; and (g) stapling the first and second portions of the colon together.

Example 19

The method of Example 18, wherein drawing the first severed end portion inwardly toward the rod further comprises cinching the first severed end portion toward the rod.

Example 20

The system of any one or more of Examples 18 through 19, wherein severing and stapling the first portion of the colon further comprises implanting a suture onto the first severed end portion such that the suture is configured to act as a purse string, wherein the act of drawing the first severed end portion inwardly toward the rod comprises pulling the implanted suture.

IV. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Suture retainer for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising a staple cartridge, wherein the staple cartridge comprises:
   (a) a plurality of staples;
   (b) a deck configured to contact tissue, wherein the deck comprises:
      (i) a slot, and
      (ii) a plurality of openings, wherein each opening of the plurality of openings is associated with a corresponding staple of the plurality of staples, such that each staple is configured to pass through a corresponding opening of the plurality of openings; and
   (c) a cinching feature positioned on the deck, wherein the cinching feature comprises:

(i) a first suture positioned on the deck wholly on a first side of the slot and covering at least one of the staple openings, and
(ii) a second suture positioned on the deck wholly on a second side of the slot and covering at least one of the staple openings,
wherein the cinching feature is configured to be coupled to tissue by the staples in response to actuation of the staple cartridge such that the staples capture the first and second sutures against the tissue, wherein the first and second sutures are configured to separate from the deck after being coupled to the tissue by the staples,
wherein the cinching feature is configured to cinch a portion of the stapled tissue radially inwardly to a cinched position relative to a distal end portion of a surgical stapling instrument.

2. The apparatus of claim 1, wherein the first suture covers multiple staple openings on the first side of the slot, wherein the second suture covers multiple staple openings on the second side of the slot.

3. The apparatus of claim 2, wherein the first suture extends over each of the staple openings on the first side of the slot, wherein the second suture extends over each of the staple openings on the second side of the slot.

4. The apparatus of claim 2, wherein the cinching feature further comprises a plurality of suture retainers operably coupled to at least one of the first suture or the second suture.

5. The apparatus of claim 1, wherein the cinching feature is adhered to the deck.

6. The apparatus of claim 1, wherein the cinching feature comprises a buttress disposed on the deck.

7. The apparatus of claim 6, wherein the buttress comprises at least one suture coupled thereto.

8. The apparatus of claim 6, wherein the buttress comprises a proximal end and a distal end, wherein the proximal end includes a pair of opposing sutures and the distal end includes a pair of opposing sutures.

9. The apparatus of claim 6, wherein the buttress is configured to be severed in response to activation of the severing and stapling assembly.

10. The apparatus of claim 6, wherein the buttress comprises at least one aperture.

11. The apparatus of claim 6, wherein the buttress comprises a proximal end and a distal end, wherein the proximal end includes a pair of opposing apertures and the distal end includes a pair of opposing apertures.

12. The apparatus of claim 1, further comprising a circular stapler, wherein the circular stapler comprises:
(i) an anvil, and
(ii) a stapling head assembly, wherein the stapling head assembly comprises:
(A) a rod configured to engage the anvil,
(B) a knife member configured to form a circular cut line in tissue, and
(C) a staple driver,
wherein the anvil and stapling head assembly are configured to cooperate to clamp and staple tissue;
wherein the cinching feature is configured to be coupled to the rod when the circular stapler is associated with tissue stapled and severed by the apparatus.

13. The apparatus of claim 12, wherein the rod includes an aperture configured to receive a portion of the cinching feature.

14. The apparatus of claim 12, wherein the rod includes at least one hook configured to engage a portion of the cinching feature.

15. A surgical system comprising:
(a) a first stapler having a staple cartridge that comprises:
(i) a plurality of staples,
(ii) a deck having a plurality of openings, wherein each opening is associated with a respective one of the staples such that each staple is configured to pass through a respective opening,
(ii) a cinching feature positioned on the deck,
wherein the staple cartridge is actuatable to staple the tissue and thereby couple the cinching feature with the tissue; and
(b) a second stapler, comprising:
(i) an anvil, and
(ii) a stapling head assembly configured to couple with the anvil, wherein the stapling head assembly comprises:
(A) a rod configured to engage the anvil, and
(B) a coupling feature provided on the rod, wherein the coupling feature is configured to engage a portion of the cinching feature,
wherein the cinching feature is configured to cinch a portion of the tissue toward the rod,
wherein the rod is retractable to clamp the tissue having the cinching feature between the anvil and the stapling head assembly,
wherein the stapling head is actuatable to staple and sever the tissue having the cinching feature.

16. The apparatus of claim 15, wherein the second stapler comprises a circular stapler.

17. The apparatus of claim 15, wherein the coupling feature comprises an aperture.

18. The apparatus of claim 15, wherein the coupling feature comprises a hook.

19. An apparatus comprising a staple cartridge, wherein the staple cartridge comprises:
(a) a plurality of staples;
(b) a deck having a plurality of openings, wherein each opening is associated with a respective one of the staples such that each staple is configured to pass through a respective opening; and
(c) a cinching feature positioned on the deck, wherein the cinching feature comprises:
(i) a suture, wherein the suture is positioned to cover at least one of the openings, and
(ii) a plurality of suture retainers coupled to the suture,
wherein the staple cartridge is actuatable to staple the tissue with the staples and thereby couple the cinching feature with the tissue,
wherein the suture is slidable relative to the suture retainers to cinch a portion of the stapled tissue toward an inwardly cinched position.

20. The apparatus of claim 1, wherein the first suture and the second suture are positioned directly on the deck.

* * * * *